US012327625B2

(12) United States Patent
Kanan

(10) Patent No.: US 12,327,625 B2
(45) Date of Patent: Jun. 10, 2025

(54) SYSTEMS AND METHODS TO PROCESS ELECTRONIC IMAGES TO IDENTIFY TUMOR SUBCLONES AND RELATIONSHIPS AMONG SUBCLONES

(71) Applicant: PAIGE.AI, Inc., New York, NY (US)

(72) Inventor: Christopher Kanan, Pittsford, NY (US)

(73) Assignee: Paige.AI, Inc., New York, NY (US)

( * ) Notice: Subject to any disclaimer, the term of this patent is extended or adjusted under 35 U.S.C. 154(b) by 335 days.

(21) Appl. No.: 17/822,989

(22) Filed: Aug. 29, 2022

(65) Prior Publication Data

US 2023/0116379 A1 Apr. 13, 2023

Related U.S. Application Data

(60) Provisional application No. 63/261,578, filed on Sep. 24, 2021.

(51) Int. Cl.
*G16H 30/20* (2018.01)
(52) U.S. Cl.
CPC .................................. *G16H 30/20* (2018.01)
(58) Field of Classification Search
None
See application file for complete search history.

(56) References Cited

U.S. PATENT DOCUMENTS

| 11,182,900 B2 | 11/2021 | Dogdas et al. |
| 11,308,616 B2 | 4/2022 | Lentini et al. |
| 2017/0091527 A1 | 3/2017 | Sarachan et al. |
| 2019/0147592 A1* | 5/2019 | Yu .................. G06V 20/695 382/128 |
| 2021/0279870 A1 | 9/2021 | Barnes et al. |
| 2022/0051047 A1 | 2/2022 | Kanan et al. |

OTHER PUBLICATIONS

"Response evaluation criteria in solid tumors," Wikipedia, Retrieved from https://en.wikipedia.org/wiki/Response_evaluation_criteria_in_solid_tumors (6 pages).
"Tumour heterogeneity" Wikipedia. Retrieved from https://en.wikipedia.org/wiki/Tumour_heterogeneity (18 pages).
(Continued)

*Primary Examiner* — Leon Flores
(74) *Attorney, Agent, or Firm* — Bookoff McAndrews, PLLC

(57) ABSTRACT

A computer-implemented method for detecting tumor subclones may include receiving one or more digital images into a digital storage device, the one or more digital images including images of a tumor of a patient, detecting one or more neoplasms in the one or more received digital images for each patient, extracting one or more visual features from each detected neoplasm, determining a hierarchy dendrogram based on the detected one or more neoplasms and the extracted one or more visual features for each detected neoplasm, determining one or more leaf nodes based on the determined hierarchy dendrogram, and determining whether there are two or more neoplasms among the detected one or more neoplasms that originated independently.

20 Claims, 17 Drawing Sheets

(56) References Cited

OTHER PUBLICATIONS

Ramón y Cajal, S. et al., "Clinical implications of intratumor heterogeneity: challenges and opportunities." Journal of Molecular Medicine 98.2, 161-177 (2020).

Rubert, D. "Distance and Similarity Measures in Comparative Genomics." Diss. Universidade Federal de Mato Grosso do Sul, 2019 (116 pages).

Xie, X., Guan, J. & Zhou, S. "Similarity evaluation of DNA sequences based on frequent patterns and entropy." BMC Genomics 16 (Suppl 3), S5 (2015) (10 pages).

Zhao, C., Wang, Z. "GOGO: An improved algorithm to measure the semantic similarity between gene ontology terms." Scientific Reports 8, 15107 (2018) (10 pages).

Mahrooghy, Majid, et al. "Pharmacokinetic tumor heterogeneity as a prognostic biomarker for classifying breast cancer recurrence risk." IEEE Transactions on Biomedical Engineering 62.6, Jun. 1, 2015, pp. 1585-1594.

\* cited by examiner

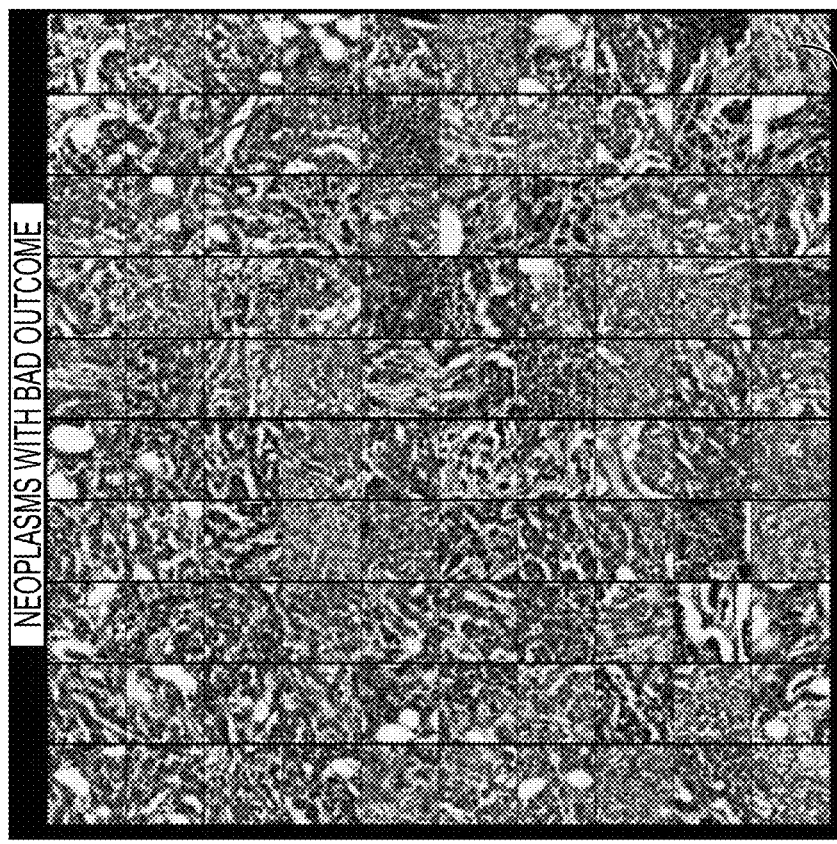
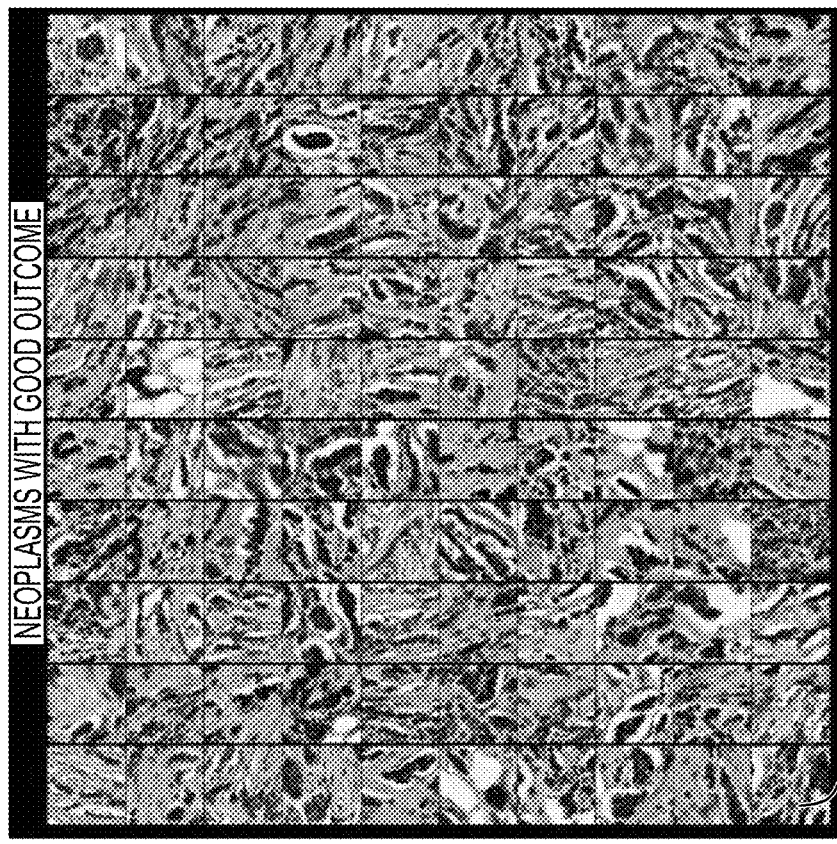
FIG. 11A
FIG. 11B

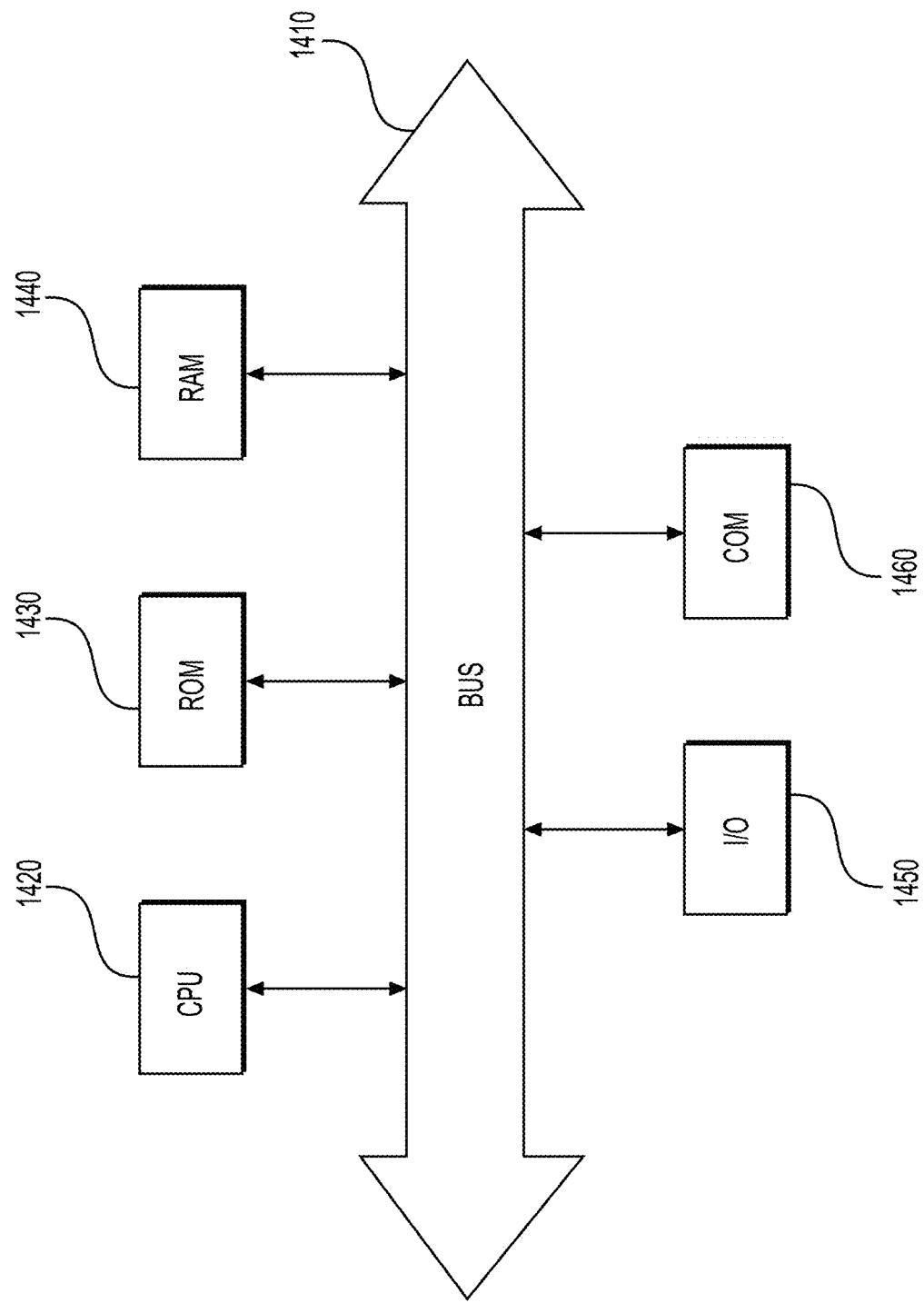

SYSTEMS AND METHODS TO PROCESS ELECTRONIC IMAGES TO IDENTIFY TUMOR SUBCLONES AND RELATIONSHIPS AMONG SUBCLONES

RELATED APPLICATION(S)

This application claims priority to U.S. Provisional Application No. 63/261,578, filed Sep. 24, 2021, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods to identify tumor subclones and relationships among subclones.

BACKGROUND

Neoplastic cells often mutate over time to spread more efficiently or to become resistant to treatment. As a tumor continues to mutate, multiple sub-clones may have differing mutations. This phenomena is known as tumor heterogeneity. A major challenge in genomic profiling of tumors is that often, only a single sub-clone may be profiled. In addition, multiple sub-clones may be intermingled when a sample is taken from the tumor for genomic sequencing, resulting in inaccurate information.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for detecting tumor subclones.

In one embodiment, a computer-implemented method is disclosed for detecting tumor subclones, the method comprising: receiving one or more digital images into a digital storage device, the one or more digital images including images of a tumor of a patient, detecting one or more neoplasms in the one or more received digital images for each patient, extracting one or more visual features from each detected neoplasm, determining a hierarchy dendrogram based on the detected one or more neoplasms and the extracted one or more visual features for each detected neoplasm, determining one or more leaf nodes based on the determined hierarchy dendrogram, and determining whether there are two or more neoplasms among the detected one or more neoplasms that originated independently.

In accordance with another embodiment, a system is disclosed for detecting tumor subclones, the system comprising: a data storage device storing instructions for detecting tumor subclones in an electronic storage medium; and a processor configured to execute the instructions to perform a method including: receiving one or more digital images into a digital storage device, the one or more digital images including images of a tumor of a patient, detecting one or more neoplasms in the one or more received digital images for each patient, extracting one or more visual features from each detected neoplasm, determining a hierarchy dendrogram based on the detected one or more neoplasms and the extracted one or more visual features for each detected neoplasm, determining one or more leaf nodes based on the determined hierarchy dendrogram, and determining whether there are two or more neoplasms among the detected one or more neoplasms that originated independently.

In accordance with another embodiment, a non-transitory machine-readable medium storing instructions that, when executed by the a computing system, causes the computing system to perform a method for detecting tumor subclones, the method including: receiving one or more digital images into a digital storage device, the one or more digital images including images of a tumor of a patient, detecting one or more neoplasms in the one or more received digital images for each patient, extracting one or more visual features from each detected neoplasm, determining a hierarchy dendrogram based on the detected one or more neoplasms and the extracted one or more visual features for each detected neoplasm, determining one or more leaf nodes based on the determined hierarchy dendrogram, and determining whether there are two or more neoplasms among the detected one or more neoplasms that originated independently.

Additional objects and advantages of the disclosed embodiments will be Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only, and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 11A and 11B illustrate a clustering of neoplasms according to modeled outcome or treatment response, according to an exemplary technique presented herein.

FIG. 14 depicts an exemplary system that may execute techniques presented herein.

DESCRIPTION OF THE EMBODIMENTS

Figure 1A:
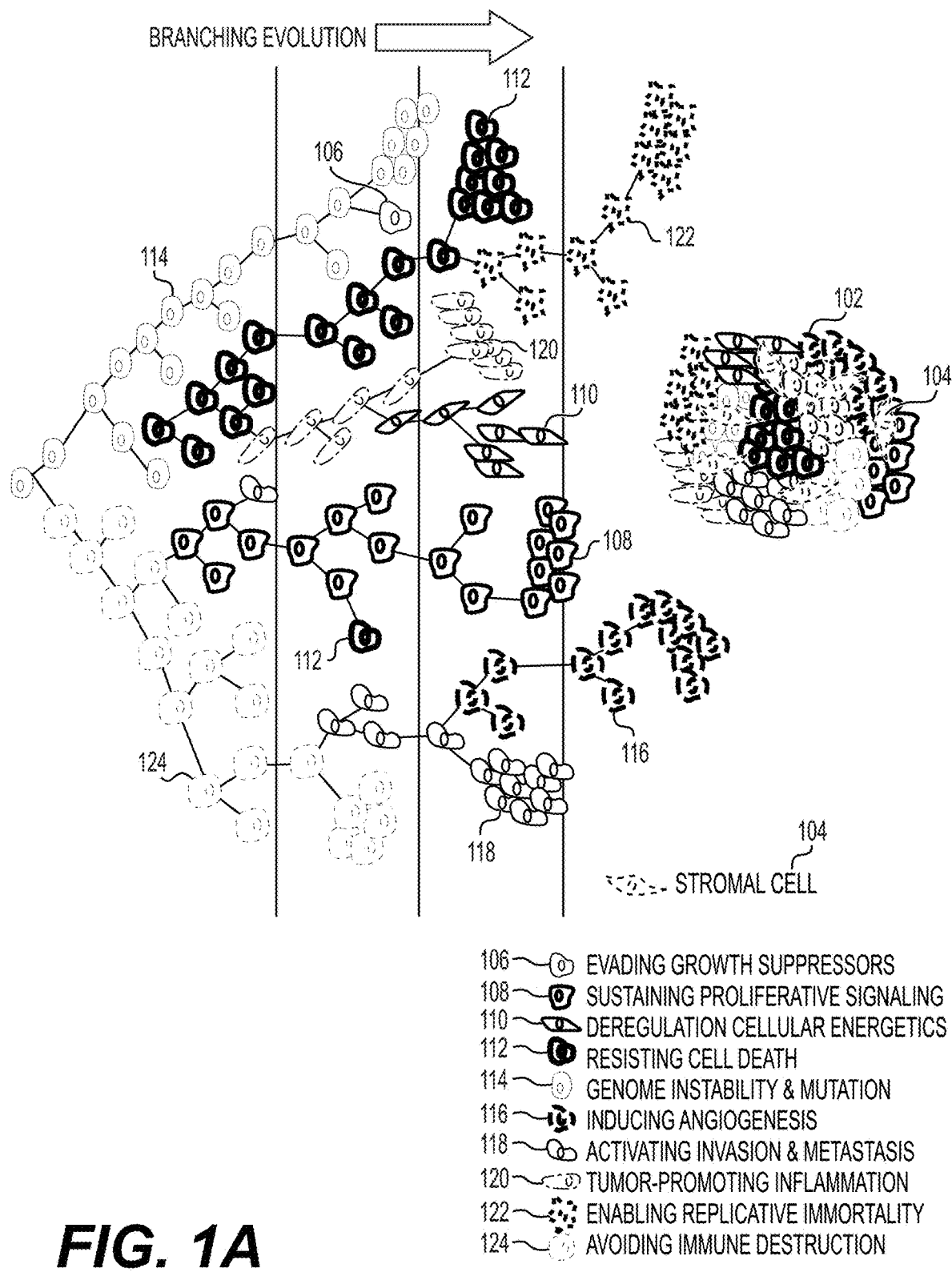
FIG. 1A illustrates heterogeneity of tumor cells.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Techniques presented herein describe an AI-based method for detecting or identifying tumor sub-clones from pathology images, enabling targeted spatial profiling, predicting outcomes, and/or facilitating treatment. Techniques presented herein describe AI-based methods for detecting genetically distinct tumor populations in digital pathology images and for recommending treatments best suited for an entire population.

Referring to FIG. 1A, tumors may not be made up of a single population of identical tumor cells but instead exhibit heterogeneity. That is, the tumor may be comprised of multiple dissimilar or diverse cell types. This heterogeneity may be caused, for example, by the tumor exhibiting branched evolution to acquire a multitude of distinct mutations (subclones), some of which may result in the tumor becoming metastatic and therefore spreading outside of a primary organ in which the tumor originated.

Figure 1B:
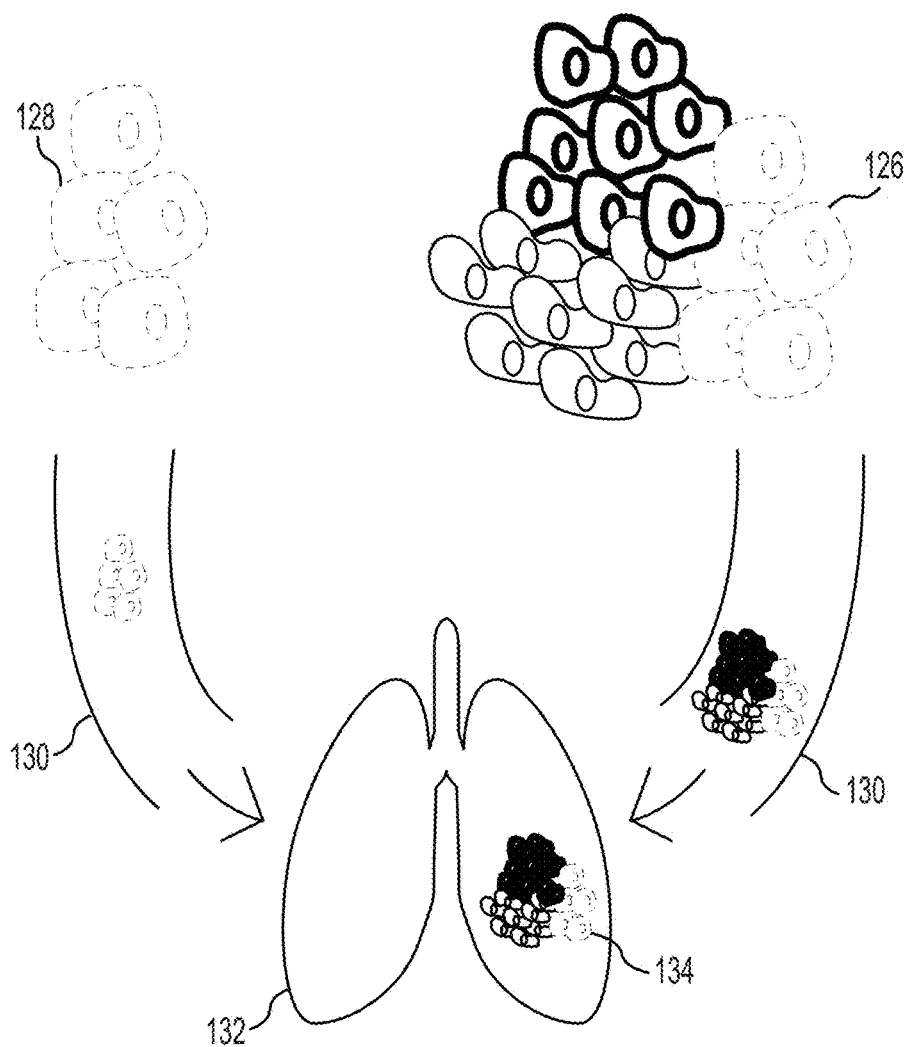
FIG. 1B illustrates tumor metastasis.

Tumors in a patient are often subclones of each other, such that the patient may have multiple tumor populations with distinct sets of mutations. While a patient could have multiple tumors that arise independently, a single tumor cell may mutate multiple times, resulting in multiple tumor populations with differing morphologic and genomic profiles. For example, a tumor 102 may comprise, in addition to stromal cells 104, subclone cells exhibiting characteristics and malignant features such as, for example, evading growth suppressors 106, sustaining proliferative signaling 108, deregulation cellular energetics 110, resisting cell death 112, genome instability & mutation 114, inducing angiogenesis 116, activating invasion & metastasis 118, tumor-promoting inflammation 120, enabling replicative mortality 122, and avoiding immune destruction 124. FIG. 1B illustrates metastatic spread of tumors 126 and 128 through a patient's blood vessels 130 to the patient's lungs 132 to form a metastatic tumor 134. (FIGS. 1A and 1B adapted from Cajal, et al., Clinical implications of intratumor heterogeneity: challenges and opportunities. *J Mol Med* 98, 161-177 (2020)).

Thus, understanding the clones and subclone cells present in a tumor may be important to the diagnosis and treatment of the disease. Identification of tumor subclones may be performed by methods including sequencing multiple tumors in distinct spatial locations. However, such a sequencing process may be expensive, time consuming, and error prone. As a result, in current practice, this kind of profiling may be typically limited to research purposes rather than benefitting individual patients.

As discussed above, tumor clones may have distinct morphologic and genomic profiles such that each population may potentially need distinct treatments. If a treatment only eliminates one clone, but not all clones, the patient may continue to have disease despite temporary shrinkage of some of the tumors.

Techniques disclosed herein may use artificial intelligence (AI) to identify genetically distinct tumors in digital pathology images and to subsequently identify traits about each of the identified tumors, including their subclonal relationships to each other.

Techniques disclosed herein may detect neoplasms on a slide. Techniques disclosed herein may also categorize the detected neoplasms into distinct sub-clonal populations. This categorization may be performed at a macro-level (e.g., tiles, polygons, etc.) or at a cellular-level. Techniques disclosed herein may use or operate on digital pathology images, which may include, for example, image data such as whole slide images of pathology data, radiology scans, etc.

Figure 2A:
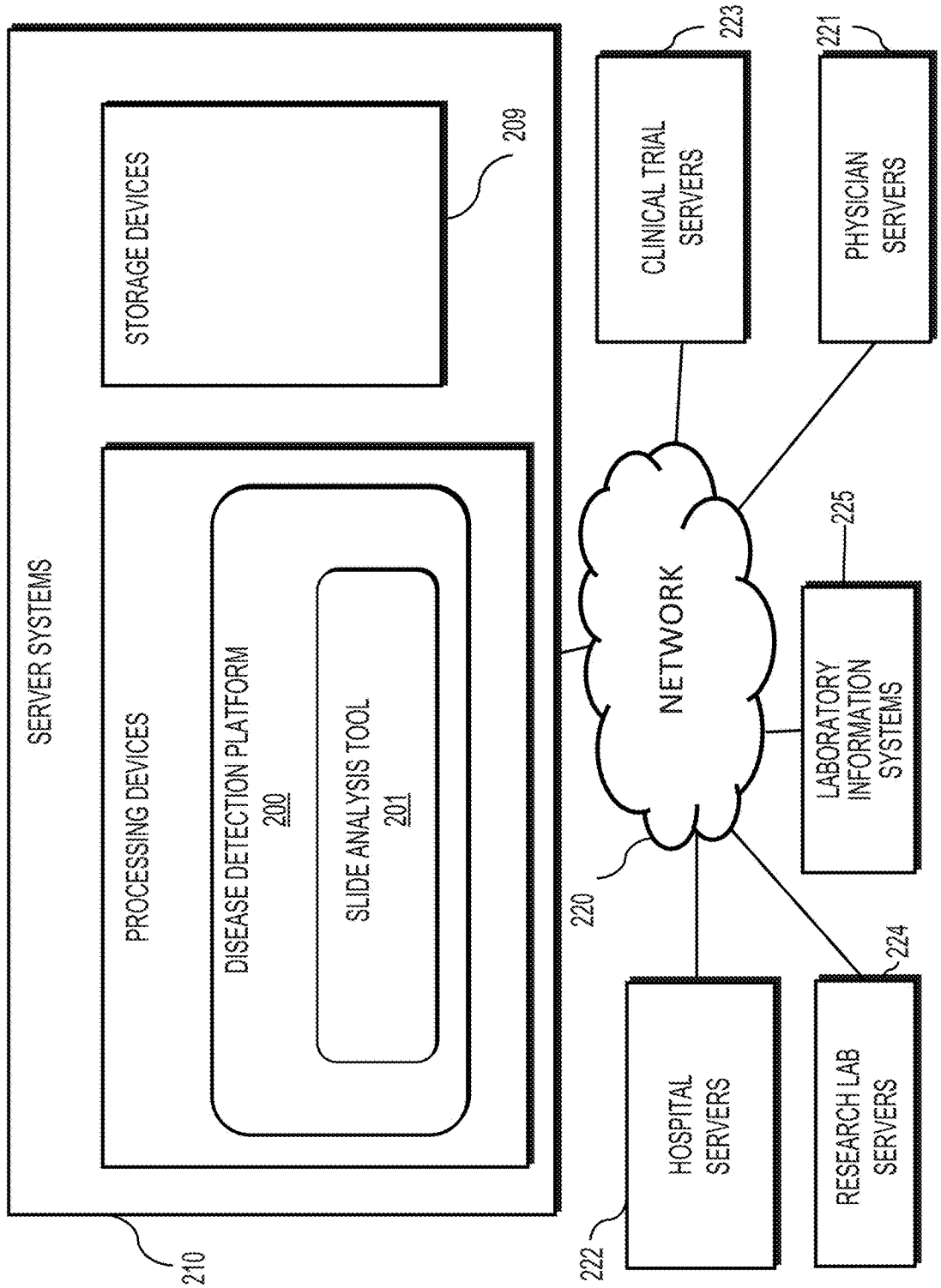
FIG. 2A illustrates an exemplary block diagram of a system and network for identifying neoplasms and/or diagnosing a disease (e.g., cancer) from electronic or digital slide images, according to an exemplary technique presented herein.
Figure 2B:
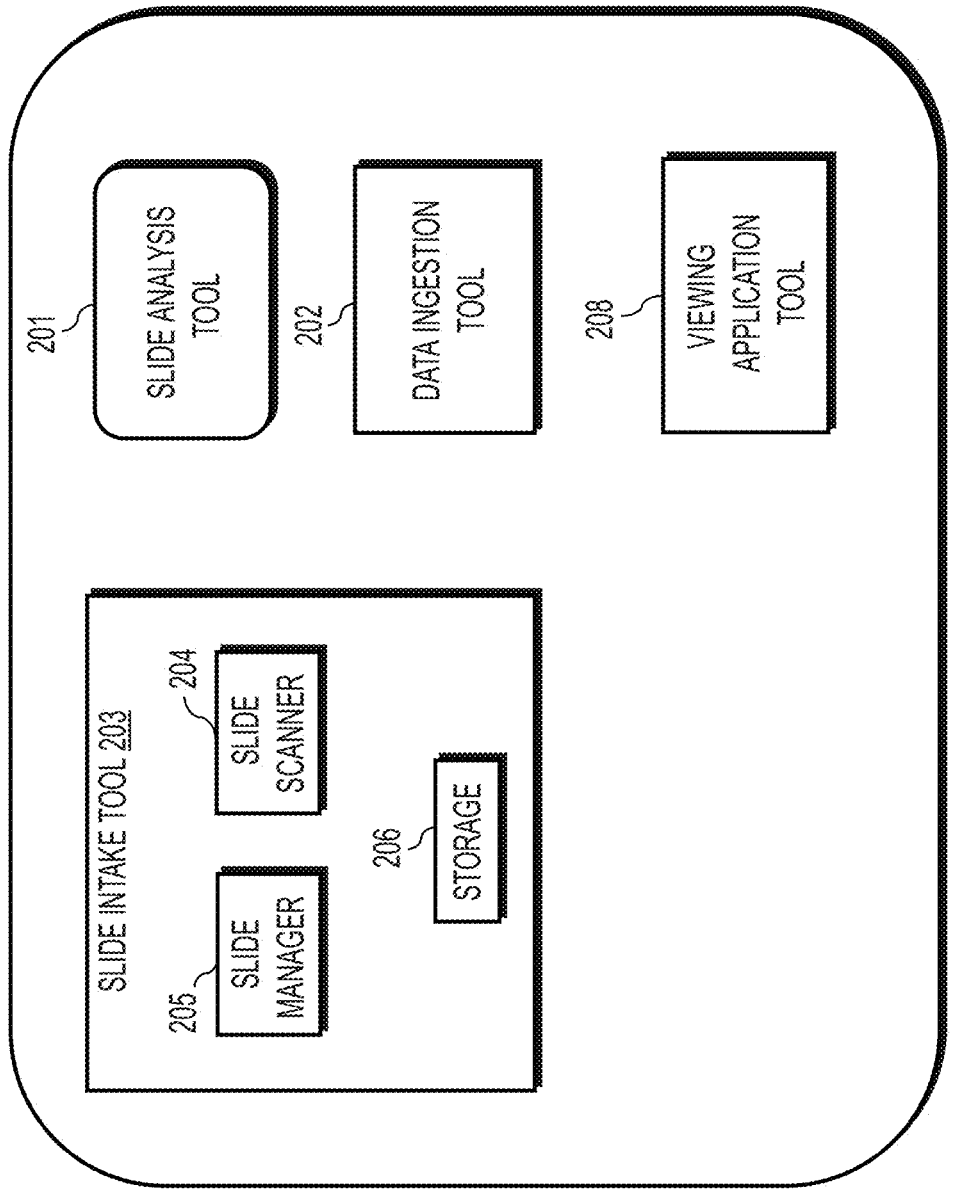
FIG. 2B illustrates an exemplary block diagram of a disease detection platform, according to an exemplary technique presented herein.
Figure 2C:
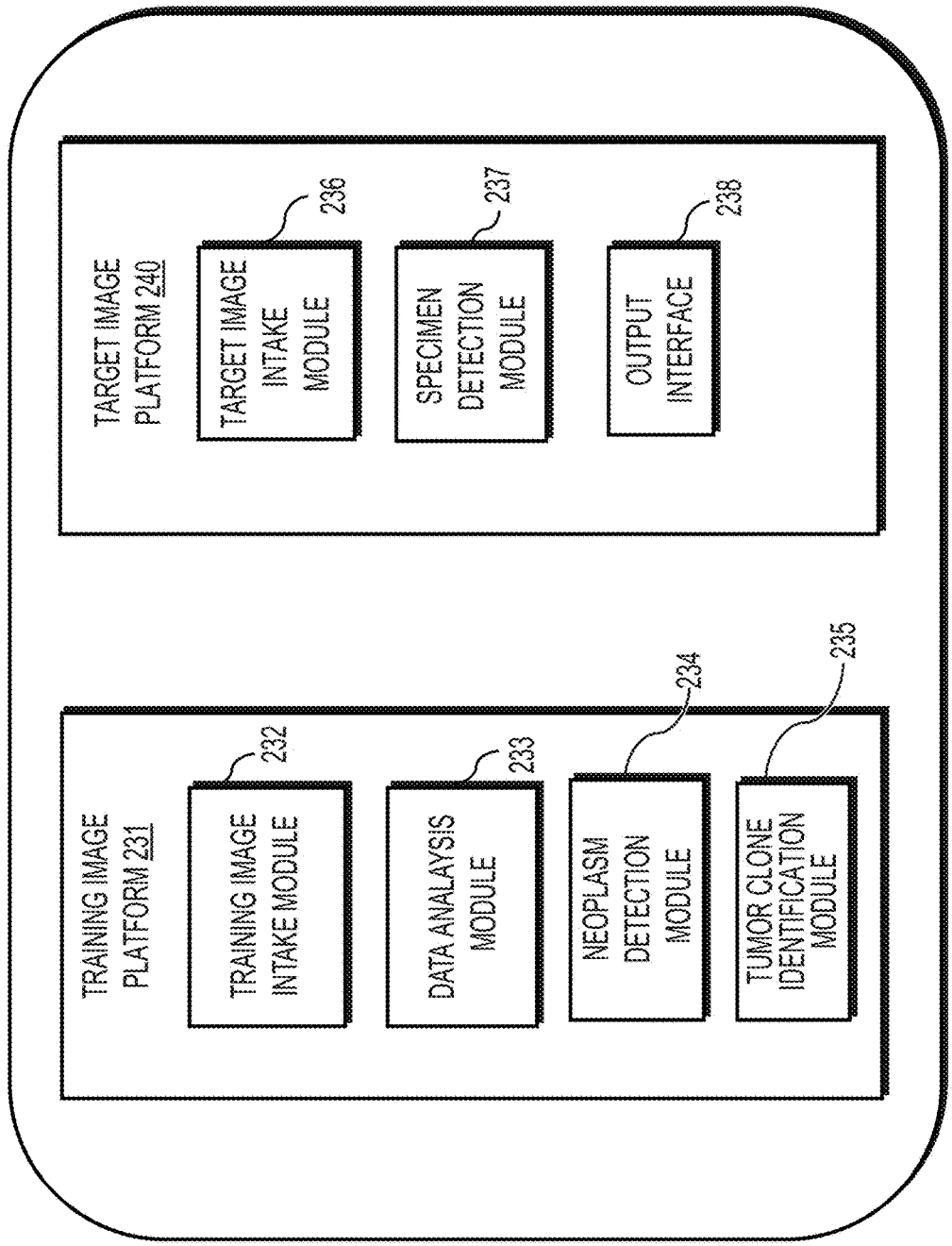
FIG. 2C illustrates an exemplary block diagram of a slide analysis tool, according to an exemplary technique presented herein.

FIGS. 2A through 2C illustrate a system and network to identify neoplasms and/or diagnose a disease (e.g., cancer) from image data such as electronic or digital slide images according to an exemplary technique of the present disclosure.

Specifically, FIG. 2A illustrates an electronic network 220 that may be connected to servers at hospitals, research laboratories, and/or doctor's offices, etc. For example, physician servers 221, hospital servers 222, clinical trial servers 223, research lab servers 224, and/or laboratory information systems 225, etc., may each be connected to an electronic network 220, such as the Internet, through one or more computers, servers and/or handheld mobile devices. According to an exemplary technique of the present application, the electronic network 220 may also be connected to server systems 210, which may include processing devices that are configured to implement a disease detection platform 200, which may include a slide analysis tool 201 for determining specimen property or image property information pertaining to digital pathology image(s), and using machine learning to determine whether a disease or infectious agent is present, according to an exemplary technique of the present disclosure.

The slide analysis tool 201 may allow for rapid evaluation of the composition of tumor tissue detected in pathology images, such as the presence of one or more cell clones or subclones, facilitate the diagnosis of disease such as from the determined tumor composition, and prediction of disease outcome. The slide analysis tool 201 may be configured to detect neoplasms, tumor sublones, and/or mutations, and the disease detection platform 200 may use detected neoplasms to diagnose diseases, such as cancer.

The physician servers 221, hospital servers 222, clinical trial servers 223, research lab servers 224 and/or laboratory information systems 225 may create or otherwise obtain images of one or more patients' cytology specimen(s), histopathology specimen(s), slide(s) of the cytology specimen(s), digital pathology images of the slide(s) of the histopathology specimen(s), or any combination thereof. The physician servers 221, hospital servers 222, clinical trial servers 223, research lab servers 224 and/or laboratory information systems 225 may also obtain any combination of patient-specific information, such as age, medical history, cancer treatment history, family history, past biopsy or cytology information, etc. The physician servers 221, hospital servers 222, clinical trial servers 223, research lab servers 224 and/or laboratory information systems 225 may transmit digital slide images and/or patient-specific information to server systems 210 over the electronic network 220. Server system(s) 210 may include one or more storage devices 209 for storing images and data received from at least one of the physician servers 221, hospital servers 222, clinical trial servers 223, research lab servers 224, and/or laboratory information systems 225. Server systems 210 may also include processing devices for processing images and data stored in the storage devices 209. Server systems 210 may further include one or more machine learning tool(s) or capabilities. For example, the processing devices may include a machine learning tool for a disease detection platform 200, according to one technique. Alternatively or in addition, techniques of the present disclosure (or portions of the system and methods of the present disclosure) may be performed on a local processing device (e.g., a desktop computer, a laptop, a tablet, a mobile device, etc.).

The physician servers 221, hospital servers 222, clinical trial servers 223, research lab servers 224 and/or laboratory information systems 225 refer to systems used by pathologists for reviewing the images of the slides. In hospital settings, tissue type information may be stored in a laboratory information system 225.

FIG. 2B illustrates an exemplary block diagram of a disease detection platform 200 for detecting disease, such as types cancer, from digital pathology image(s) of tumor specimens using machine learning. The disease detection platform 200 may include a slide analysis tool 201, a data ingestion tool 202, a slide intake tool 203, a slide scanner 204, a slide manager 205, a storage 206, and a viewing application tool 208.

The slide analysis tool 201, as described below, refers to a process and system for detecting disease, such as types cancer, from digital pathology image(s) of tumor specimens. Machine learning may be used to classify cell types, such as clones and subclones, found in an image, according to an exemplary technique. The slide analysis tool 201 may also determine relationships among the cell clones and subclones, and predict disease outcome based on tumor composition, as described in the techniques discussed below.

The data ingestion tool 202 refers to a process and system for facilitating a transfer of the digital pathology images to the various tools, modules, components, and devices that are used for classifying and processing the digital pathology images, according to an exemplary technique.

The slide intake tool 203 refers to a process and system for scanning pathology images and converting them into a digital form, according to an exemplary technique. The slides may be scanned with slide scanner 204, and the slide manager 205 may process the images on the slides into digital pathology images and store the digital pathology images in storage 206. Alternatively, digital pathology images may be received from any of the servers discussed above with respect to FIG. 2A, and stored in storage 206. Alternatively, digital pathology images may be accessed directly in network accessible storage located remotely from disease detection platform 200 without requiring local storage of the digital pathology images in storage 206.

The viewing application tool 208 refers to a process and system for providing a user with a specimen property or image property information pertaining to digital pathology image(s), according to an exemplary technique. The information may be provided through various output interfaces (e.g., a screen, a monitor, a storage device and/or a web browser, etc.) . . . . Viewing application tool 208 may further provide for specification of user preferences, such as customization of the operation of the various controls and user interfaces disclosed herein.

The slide analysis tool 201, and one or more of its components, may transmit and/or receive digital slide images and/or patient information to server systems 210, physician servers 221, hospital servers 222, clinical trial servers 223, research lab servers 224, and/or laboratory information systems 225 over a network 220. Further, server systems 210 may include the one or more storage devices 209 for storing images and data received from at least one of the slide analysis tool 201, the data ingestion tool 202, the slide intake tool 203, the slide scanner 204, the slide manager 205, and viewing application tool 208. Server systems 210 may also include processing devices for processing images and data stored in the storage devices. Server systems 210 may further include one or more machine learning tool(s) or capabilities, e.g., due to the processing devices. Alternatively, or in addition, the present disclosure (or portions of the system and methods of the present disclosure) may be performed on a local processing device (e.g., a laptop, a tablet, a desktop computer, a smart phone, etc.).

Any of the above devices, tools, and modules may be located on a device that may be connected to an electronic network 220 such as the Internet or a cloud service provider, through one or more computers, servers and/or handheld mobile devices.

FIG. 2C illustrates an exemplary block diagram of a slide analysis tool 201, according to an exemplary technique of the present disclosure. The slide analysis tool 201 may include a training image platform 231 and/or a target image platform 240.

According to one technique, the training image platform 231 may include a training image intake module 232, a data analysis module 233, a neoplasm and/or tumor subclone detection module 234, and a tumor clone identification module 235.

The training image platform 231, according to one technique, may create or receive training images that are used to train a machine learning model to effectively analyze and classify digital pathology images and/or analyze or detect features within the digital pathology images. For example, the training images may be received from any one or any combination of the server systems 210, physician servers 221, hospital servers 222, clinical trial servers 223, research lab servers 224, and/or laboratory information systems 225. Alternatively, digital pathology images may be accessed directly in network accessible storage located remotely from training image platform 231.

Images used for training may come from real sources (e.g., humans, animals, etc.) or may come from synthetic sources (e.g., graphics rendering engines, 3D models, etc.). Examples of digital pathology images may include (a) digital slides stained with a variety of stains, such as (but not limited to) H&E, Hematoxylin alone, IHC, molecular pathology, etc.; and/or (b) digital tissue samples from a 3D imaging device, such as microCT.

The training image intake module 232 may create or receive training images that are used to train a machine learning model to effectively analyze and classify digital pathology images and/or analyze or detect features within the digital pathology images. For example, the training images may be received from any one or any combination of the server systems 210, physician servers 221, hospital servers 222, clinical trial servers 223, research lab servers 224, and/or laboratory information systems 225. The training image intake module 232 may further receive a training dataset that may include additional patient information related to each received digital pathology image. The additional information may, for example, include validated information about a location and/or type of neoplasm present in each received digital pathology image. Such data may be employed in the machine learning model training process. This dataset may be kept on a digital storage device.

The data analysis module 233 may identify whether an area of a training image belongs to a region of interest or salient region or to a background of a digital pathology image. A salient region may be a region that contains neoplasms, subtumors, or mutations.

The neoplasm detection module 234 may analyze digital pathology images to determine whether the region contains one or more neoplasms and/or neoplasm types. The identification of such may trigger an alert to a user and/or an indication that further analysis is required. Once a location and/or region of each neoplasm is determined or identified on a slide by the neoplasm detection module 234, the tumor clone identification module 235 may identify and/or determine individual clones or subclones. The identification of such may trigger an alert to a user and/or an indication that further analysis is required.

The training image platform 231, according to one technique, may use output from data analysis module 233, neoplasm detection module 234, and/or tumor clone identification module 235, to train a machine learning model, or other statistical or artificial intelligence model, to detect and/or classify neoplasms in digital pathology images. Such training may be performed, for example, by any of the techniques described below with respect to FIG. 3, 5, 7, or 9.

According to one technique, the target image platform 240 may include a target image intake module 236, a specimen detection module 237, and an output interface 238. The target image platform 240 may receive a target image and apply the trained machine learning model to the received target image to determine a characteristic of a target specimen. For example, the target image may be received from any one or any combination of the server systems 210, physician servers 221, hospital servers 222, clinical trial servers 223, research lab servers 224, and/or laboratory information systems 225. Alternatively, digital pathology images may be accessed directly in network accessible storage located remotely from training image platform 231. The target image intake module 236 may further receive a target dataset that may include additional patient information related to each received digital pathology image.

The specimen detection module 237 may apply the machine learning model to the target digital pathology images to determine whether a feature, such as, for example, one or more neoplasms of interest, is present in the target digital pathology images.

The output interface 238 may be used to output information about the target digital pathology images and the detected neoplasms of interest (e.g., to a screen, monitor, storage device, web browser, etc.). The output interface 238 may display information about identified salient regions of analyzed slides, such as any detected neoplasms of interest, according to a policy or strategy (e.g., by zooming, panning, and/or jumping) to navigate the slides. The final result or output on the output interface 238 may appear as an automated, customized video or "tour" of the slides.

Neoplasm Detection Module

Cancers are composed of neoplasms, which are abnormal masses of tissue that form when cells grow and divide more than they should or do not die when they should. Neoplasms may be benign or malignant (i.e., cancer), but it has been hypothesized that some benign neoplasms may later become malignant sub-clones of the original neoplasm. All tumors are composed of neoplasms.

A neoplasm detection module or a neoplasm detector (such as the neoplasm detection module 234 described above with reference to FIGS. 2A-2C) may categorize regions of a digital pathology image, such as into categories of regions with neoplasms vs. non-neoplasm regions. Alternatively, the neoplasm detection module may determine a kind or type of neoplasm in a region using a multi-class system (i.e., non-neoplasm vs. neoplasm type 1 vs. neoplasm type 2, etc.). As an example of the multi-class approach in the context of breast cancer, distinct outputs or classes of neoplasms may include invasive lobular carcinoma, invasive ductal carcinoma, ductal carcinoma in situ, lobular carcinoma in situ, atypical ductal hyperplasia, etc. Neoplasm detection module 234 may perform such detection with respect to specimens detected in target images, such as by specimen detection module 237.

Figure 3:
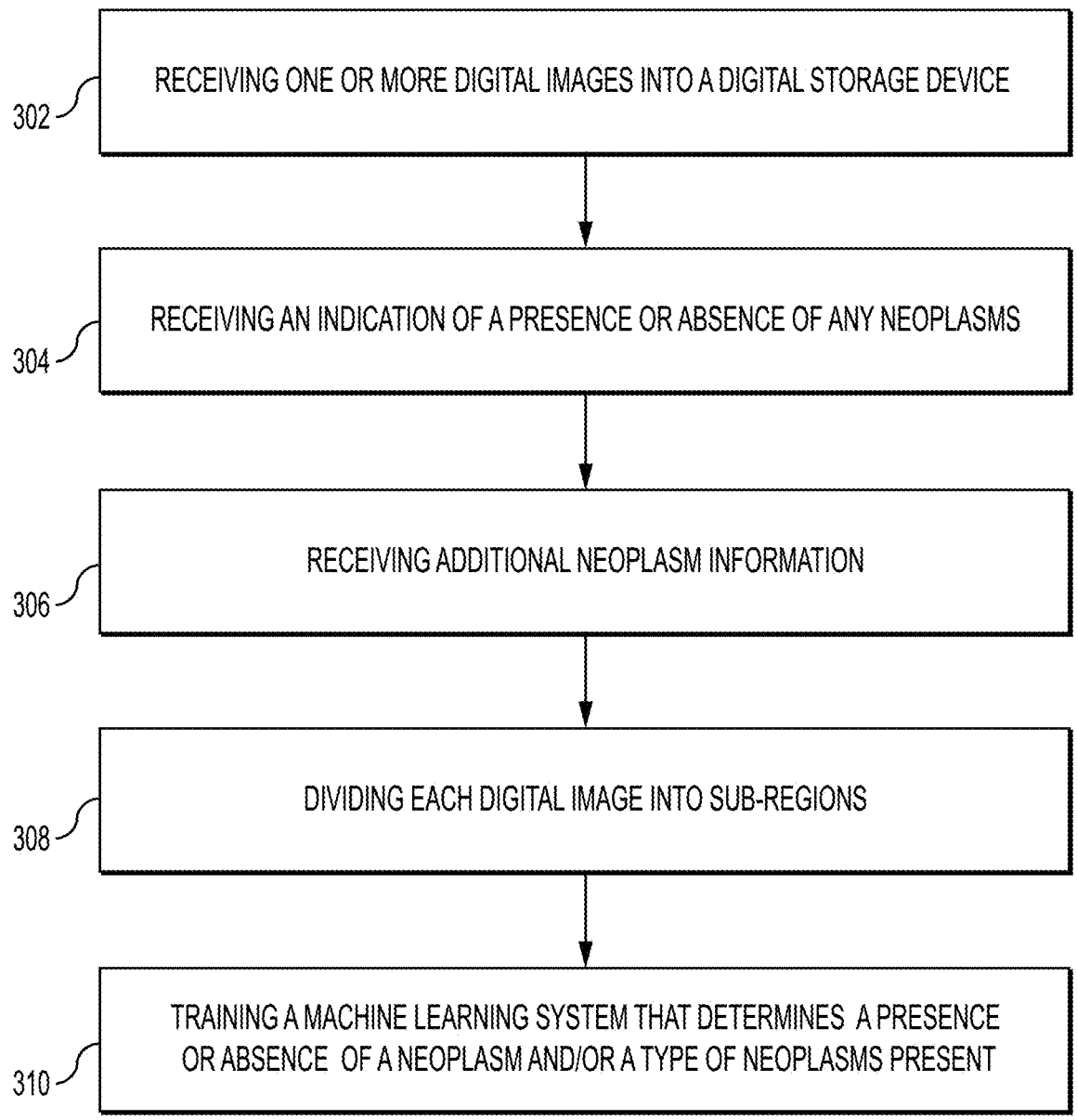
FIG. 3 is a flowchart of an exemplary method for training a neoplasm detection model, according to an exemplary technique presented herein.

Referring to FIG. 3, a method 300 of training the neoplasm detection module may include a step 302 of receiving one or more digital pathology images (e.g., histology images, whole slide images or WSIs, etc.) into a digital storage device (e.g., hard drive, network drive, cloud storage, RAM, etc., such as storage devices 209 or 206 depicted in FIGS. 2A and 2B) and a step 304 of receiving an indication of a presence or absence of any neoplasms. Steps 302 and 304 may be performed simultaneously and/or separately. For example, the received one or more digital pathology images may include additional data, such as metadata, annotations, etc., indicating the presence of neoplasms and a number of neoplasms present. Alternatively, information about a presence or absence of neoplasms in the digital pathology images may be received after further processing of the images, such as by neoplasm detection module 234. The method 300 of training the neoplasm detection module may also include a step 306 of receiving additional neoplasm information, such as information on the kinds or types of neoplasms present in the received image, the number of such neoplasms, and/or spatial locations of each neoplasm, which may be indicated with a binary pixel mask, a polygon, etc. For example, the received one or more digital pathology images may include additional data, such as metadata, annotations, etc., indicating information about the present neoplasms, such as type, location, etc. The additional neoplasm information may be received after further processing of the images, such as by neoplasm detection module 234.

The method 300 of training the neoplasm detection module may include a step 308 of breaking or dividing each digital pathology image into sub-regions. Regions may be specified in a variety of methods, including creating tiles of the image, segmentations based on edge/contrast, segmentations via color differences, segmentations based on energy minimization, supervised determination by a machine learning model, EdgeBoxes, SharpMask, etc.

The method 300 of training the neoplasm detection module may include a step 310 of training a machine learning system or model that may take, as input, for example, a digital pathology image, may infer or determine a presence or absence of a neoplasm and/or the kind or type of neoplasms present, and may, for example, compare the received neoplasm information with the inferred or determined neoplasm information. The trained system may be output to digital storage. Training of the machine learning model may be by any know methods, such as, for example, weak supervision, bounding box or polygon-based supervision, or pixel-level or voxel-level labeling, as discussed in further detail below.

Weak supervision is a branch of machine learning where noisy, limited, or imprecise sources are used to provide supervision signal for labeling large amounts of training data in a supervised learning setting. Weak supervision may include training a machine learning model (e.g., multi-layer perceptron or MLP, convolutional neural network or CNN, Transformers, graph neural network, support vector machine or SVM, random forest, etc.) such as through multiple instance learning (MIL) and/or weak labeling of the digital pathology image or a collection of digital pathology images. Weak supervision may be used even if a spatial location is not specified for an image.

Bounding box or polygon-based supervision may include training a machine learning model (e.g., region-based convolutional neural network or R-CNN, Faster R-CNN, Selective Search, etc.) such as through bounding boxes or polygons that may specify sub-regions of the digital pathology image. For example, all pixels or voxels within a bounding box or polygon may be labeled with the same category, such as, for example, non-neoplasm vs. neoplasm type 1 vs. neoplasm type 2, etc.

Pixel-level or voxel-level labeling (e.g., a semantic or instance segmentation) may include training a machine learning model (e.g., Mask R-CNN, U-Net, Fully Convolutional Neural Network, Transformers, etc.) through which individual pixels and/or voxels may be identified as being neoplasms and/or the type or kind of each neoplasm may be determined. For example, in semantic segmentation, each pixel or voxel may be labeled according to a category, such as, for example, non-neoplasm vs. neoplasm type 1 vs. neoplasm type 2, etc. Semantic segmentation does not distinguish different instances in the same category. That is, all pixels or voxels for "neoplasm type 2," for example, would be labeled together. In contrast, in instance segmentation, each neoplasm in each pixel or voxel in each category would be labeled separately. That is, pixels or voxels for "neoplasm type 2," for example, would be labeled according to that category and the particular neoplasm. Pixel-level and/or voxel-level labeling may be from a human annotator or may be from registered images.

Figure 4:
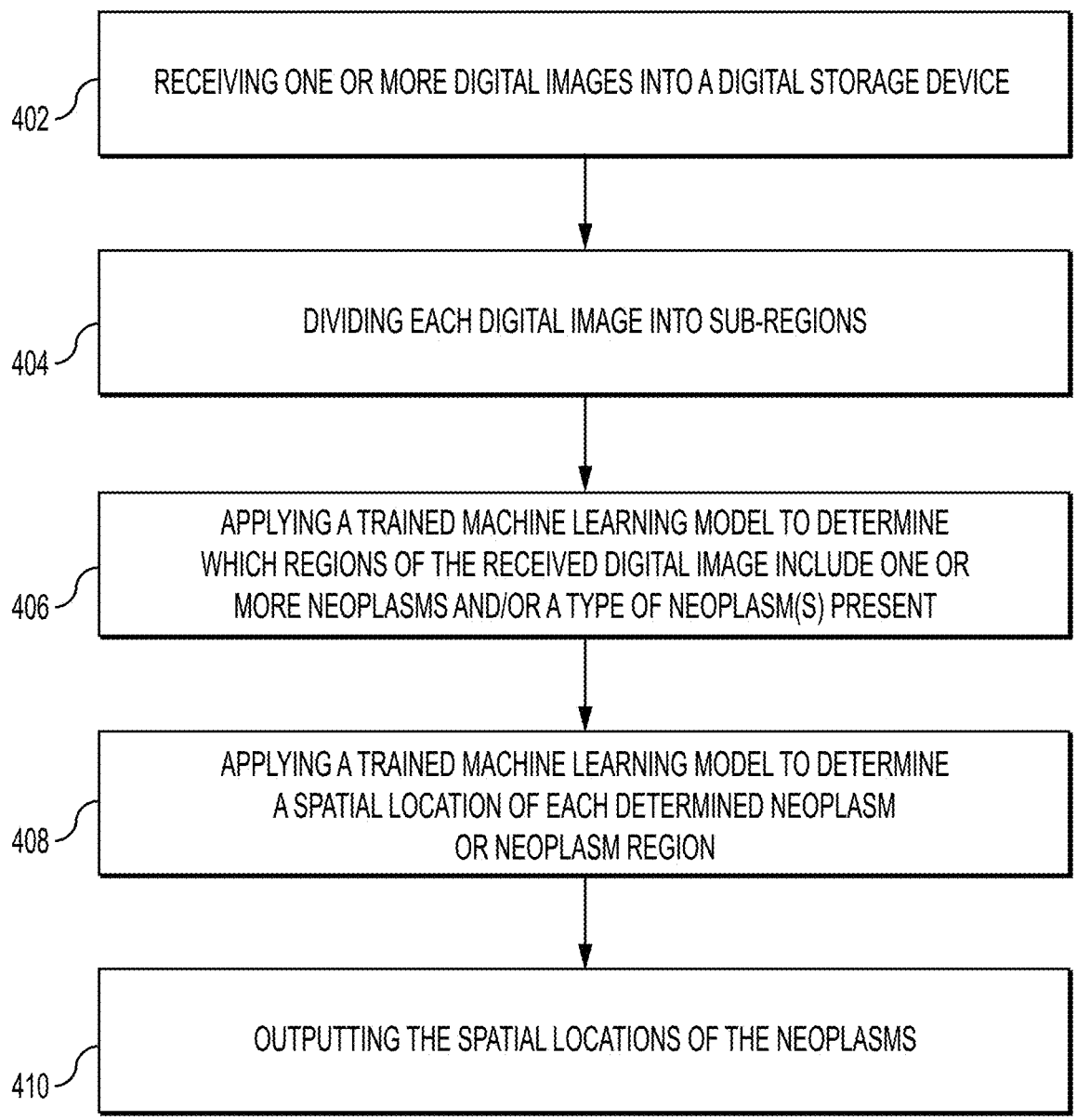
FIG. 4 is a flowchart of an exemplary method for using a neoplasm detection model, according to an exemplary technique presented herein.

Referring to FIG. 4, a method 400 of using the neoplasm detection module, such as by employing a trained machine learning model, may include a step 402 of receiving one or more digital pathology images (e.g., whole slide images or WSIs, histology images, etc.) into a digital storage device (e.g., hard drive, network drive, cloud storage, RAM, etc., such as storage devices 209 or 206 depicted in FIGS. 2A and 2B). The method 400 of using the neoplasm detection module may include a step 404 of dividing or breaking each digital pathology image into sub-regions. Regions may be specified in a variety of methods, including creating tiles of the image, segmentations based on edge/contrast, segmentations via color differences, segmentations based on energy minimization, supervised determination by a machine learning model, EdgeBoxes, SharpMask, etc. The method 400 of using the neoplasm detection module may include a step 406 of determining which regions of the received digital pathology image are neoplasms and/or a type of neoplasms present by, for example, applying a trained machine learning system, such as a machine learning system trained by the method 300 discussed above with respect to FIG. 3, to the one or more received digital pathology images.

If it is determined, in step 406, that neoplasms are present, then the method 400 of using the neoplasm detection module may include a step 408 of determining, identifying, and/or flagging spatial locations of the detected neoplasms. Determining, detecting, and/or inferring the regions may include using a variety of methods, including, but not limited to, running the machine learning model on image sub-regions to generate a determination for each sub-region and/or using machine learning visualization tools to create a detailed labeling and extracting of the relevant regions, such as, for example, a heatmap, class activation maps, etcs. The method 400 may include a step 410 of outputting the spatial locations of the neoplasms, such as, for example, data sets, images, annotations, het maps class activation maps, etc.

Tumor Clone Identification Module

Once a location and/or region of each neoplasm is determined or identified on a slide, the tumor clone identification module (such as tumor clone identification module 235 described above with reference to FIGS. 2A-2C) may be used to identify and/or determine individual clones or sub-clones. Identifying and/or determining tumor clones or subclones may be done using a variety of methods, including unsupervised clustering, supervision of sub-clonal populations, and/or supervision with outcome or treatment response. Any of the methods disclosed herein may include a step of determining clones or subclones based on, for example, detected neoplasms, leaf nodes, and/or hierarchy dendrograms. Methods of Identifying and/or determining tumor clones or subclones, according to one or more techniques, will be described in greater detail below with respect to FIGS. 5-10.

Unsupervised Clustering Method

In using unsupervised clustering to identifying tumor clones or subclones, hierarchical clustering may be used on visual features extracted from neoplasms that were identified by the neoplasm detection module to obtain a hierarchy of relationships among the neoplasms. This process may allow tumor clones to be identified within a hierarchy tree.

Unsupervised clustering may reveal morphologic characteristics and may be performed without supervised training of the system to determine the relationships. A possible advantage of a supervised approach may include improved results under some circumstances. However, gathering required data for training a supervised model may be difficult. Thus, unsupervised clustering may have advantages in some circumstances.

Figure 5:
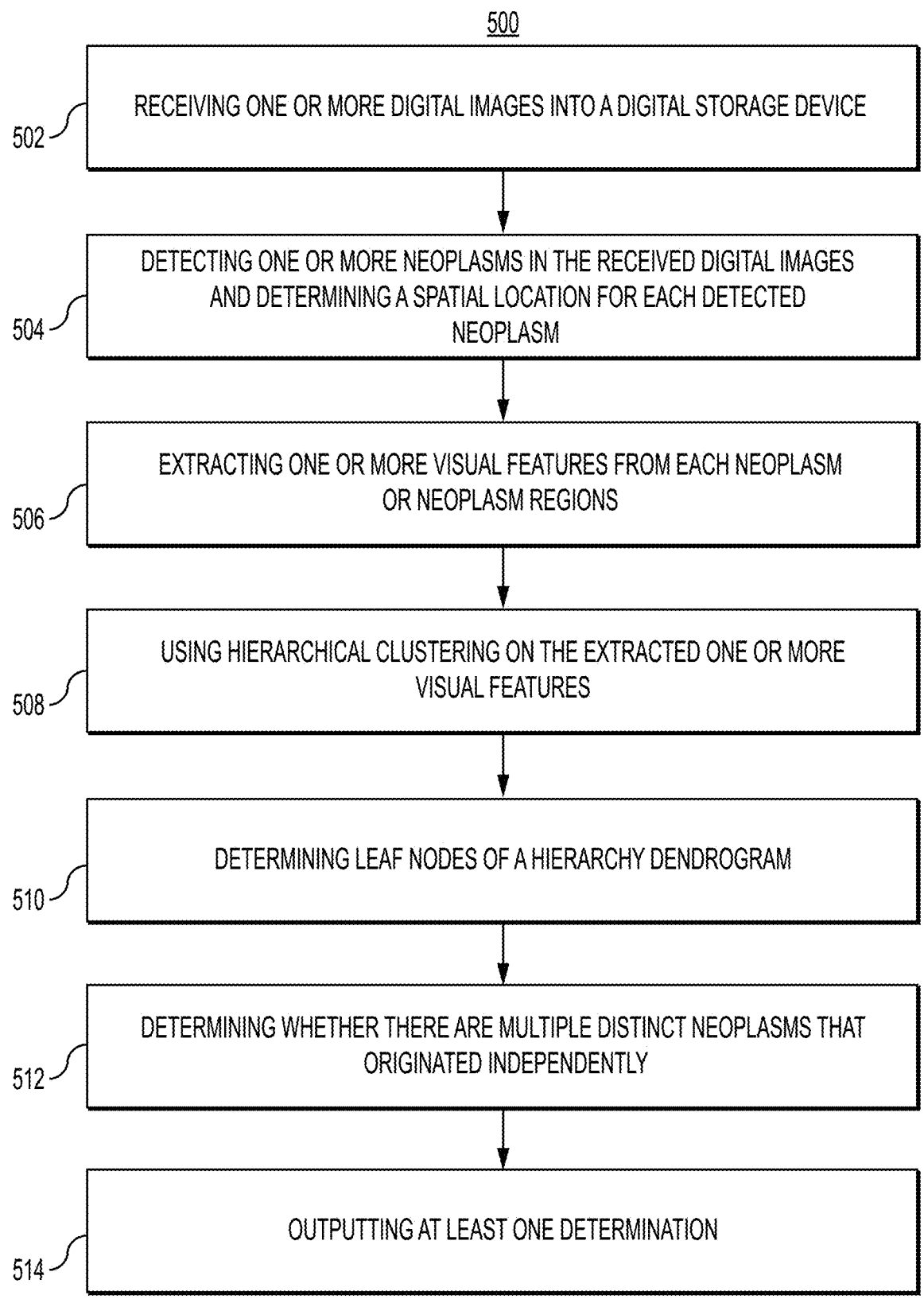
FIG. 5 is a flowchart of an exemplary method for using an unsupervised clustering method for identifying neoplasms and/or diagnosing a disease, according to an exemplary technique presented herein.

Referring to FIG. 5, a method 500 of using an unsupervised clustering method may include a step 502 of receiving one or more digital pathology images, such as, for example, digital medical or slide images (e.g., histology images or whole slide images), into a digital storage device (e.g., hard drive, network drive, cloud storage, RAM, etc.) for a patient or other subject. The method 500 of using the unsupervised clustering method may include a step 504 of detecting or identifying one or more (e.g., most or all) neoplasms on one or more received digital pathology images for the patient and determining a spatial location for each detected or identified neoplasm. Step 504 may be performed using the neoplasm detection module.

The method 500 of using the unsupervised clustering method may include a step 506 of extracting visual features (such as embeddings) from each neoplasm or neoplasm region. An embedding may be, for example, a vector or tensor representation of an input that captures information in a multi-dimensional "embedding space (i.e., a d-dimensional space) discriminative for a downstream task. Embeddings may not be human interpretable. For example, an image embedding may encode as a vector information about an N×N pixel region within an image (potentially the entire image or a local region). An example encoding may include a CNN "encoder" that transforms an image or image patch into a d-dimensional embedding. This extraction may include using raw pixel/voxel regions fed into either a hand-crafted feature extractor or a trained system for embeddings such as a convolutional neural network or a transformer which may be trained through supervised or self-supervised learning. Visual information may be transformed or converted into a vector of features that represents each neoplasm.

The method 500 of using the unsupervised clustering method may include a step 508 of using hierarchical clustering on the extracted visual features (e.g., embeddings), including, but not limited to, agglomerative clustering, divisive clustering, or Ward's clustering method. This hierarchical clustering may be used or operated directly on the embeddings using a predefined assessment of the embeddings' similarity with a given scoring method for determining how similar each embedding is to another embedding or a cluster centroid vector. Scoring methods may include Euclidean distance, cosine similarity, etc.

The method 500 of using the unsupervised clustering method may also include a step 510 of identifying or determining "leaf nodes" (e.g., the leaf nodes 604 shown in FIG. 6) of a hierarchy dendrogram in which to analyze. Identifying the leaf nodes may include thresholding the similarity score allowed in an embedding space and, if the distance is sufficiently low (e.g., less than a predetermined distance), determining a "leaf node." Thus, in a dendrogram produced via hierarchical clustering, each node may also be a d-dimensional vector. A leaf node may then be determined as one in which all members of that cluster are sufficiently close in terms of score to a centroid. An outcome of the technique may be to determine the number of tumor subclones and their genetic relationships. That is, what is the evolutionary history of each subclone with respect to each other and how different does one subclone need to be from its ancestors to call it a new subclone? The exemplary techniques may make this determination based on the visual characteristics of the individual tumor cells, which may be encoded by the embedding vectors. Exemplary leaf nodes are shown in FIG. 6.

The method 500 of using the unsupervised clustering method may include a step 512 of identifying or determining whether there are multiple (e.g., two or more) distinct neoplasms that originated independently. This determination may include "cutting" the hierarchy dendrogram at the top if the distance between two child node clusters is sufficiently large (e.g., greater than a predetermined distance) based on a threshold. Such a predetermined threshold distance may be predetermined, for example, based on expert analysis or on an orthogonal source of information, such as, for example, spatial genomics methods that indicate how genetically distinct each tumor subclone is from other tumor subclones. Step 512 may further include determining or identifying subclone populations based on the detected neoplasms, leaf nodes, distance measurements, and/or hierarchy dendrogram. Cutting of the hierarchy dendrogram may be performed individually for each branch, rather than at the top or at the same level for the entire tree. Such a per-branch cut be advantageous to identify leaf nodes, but may not yield a balanced tree structure.

The method 500 of using the unsupervised clustering method may include a step 514 of outputting the determinations and/or an analysis to digital storage and/or a display. Outputting the determinations in step 514 may include outputting an analysis (e.g., by a machine learning system, neoplasm detection module 234, tumor clone identification module 235), producing an output overlay on an image (e.g., the received digital pathology image) with each subclone population identified (e.g., with color coding, highlighting, shading, or other visual styles), and/or computing a most canonical form of each subclone. Many methods may be used to compute the most canonical form of each subclone, such as by identifying an embedding closest to an average within a cluster and displaying a corresponding region for each subclone.

Figure 6:
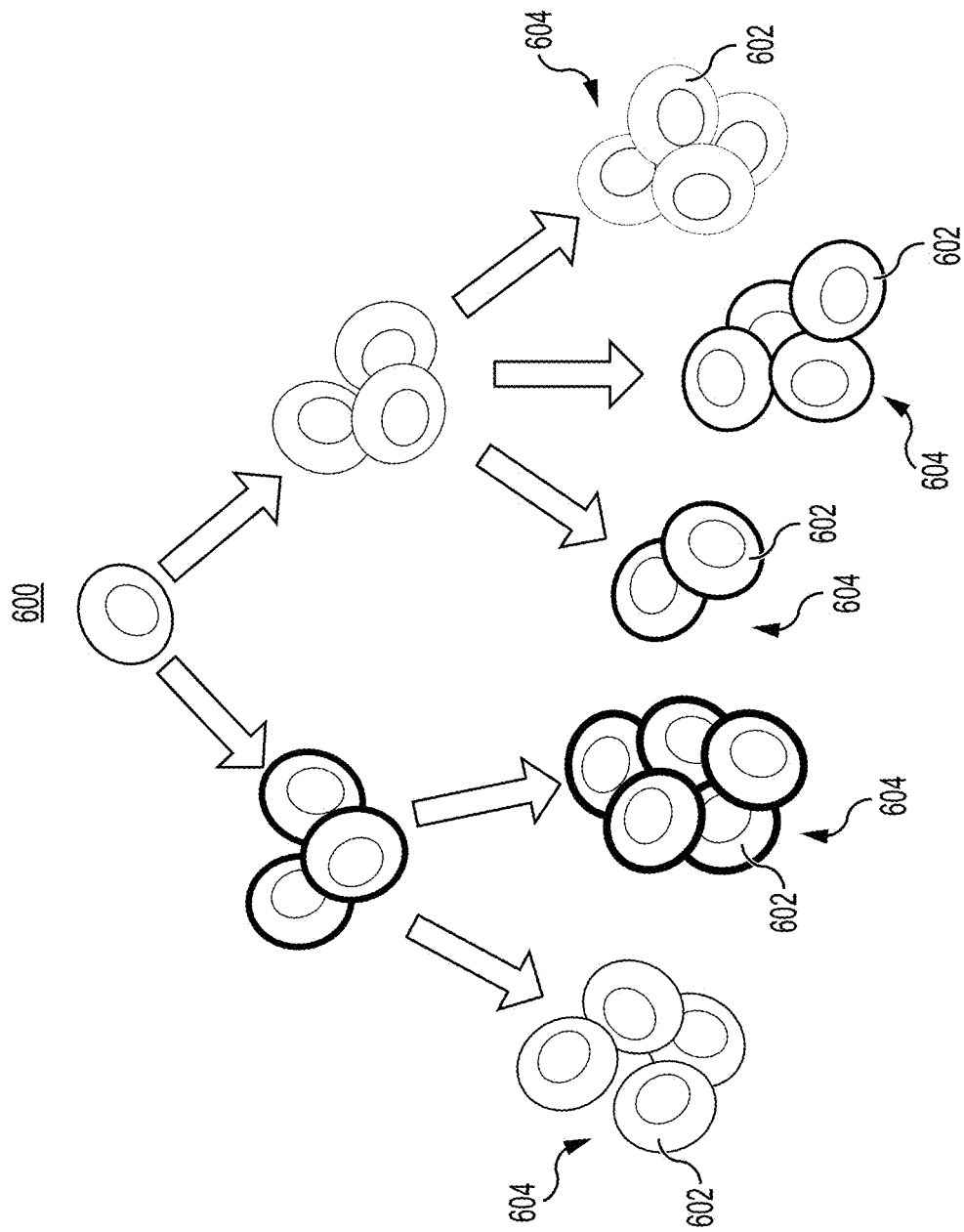
FIG. 6 illustrates a hierarchical clustering of neoplasms, according to an exemplary technique presented herein.

Referring to FIG. 6, each circle 602 in dendrogram 600 may represent visual information extracted from neoplasms. A hierarchical clustering method (such as in method 500) may produce dendrogram 600, which may be "cut" at a certain level (FIG. 6 shows a cut at level 3) to identify clusters and their relationships to each other. For example, a non-cut portion of the dendrogram may be indicated with one visual representation (e.g., a green color) and the cut areas indicated with another visual representation (e.g., a red color). Leaf nodes 604 may be visual regions assigned to the clusters at the bottom of the figure. A canonical prototype for each cluster may be visually reviewed, and the hierarchy may be evaluated to reveal the relationships among the tumor subclones. The leaf nodes 604 may be presented in visually distinct form, such as by color coding, highlighting, use of distinct line styles, or other visual styles, such that each circle 602 in a particular leaf node 604 has the same visually distinct form.

Using Supervised Learning of Sub-Clonal Populations

Figure 7:
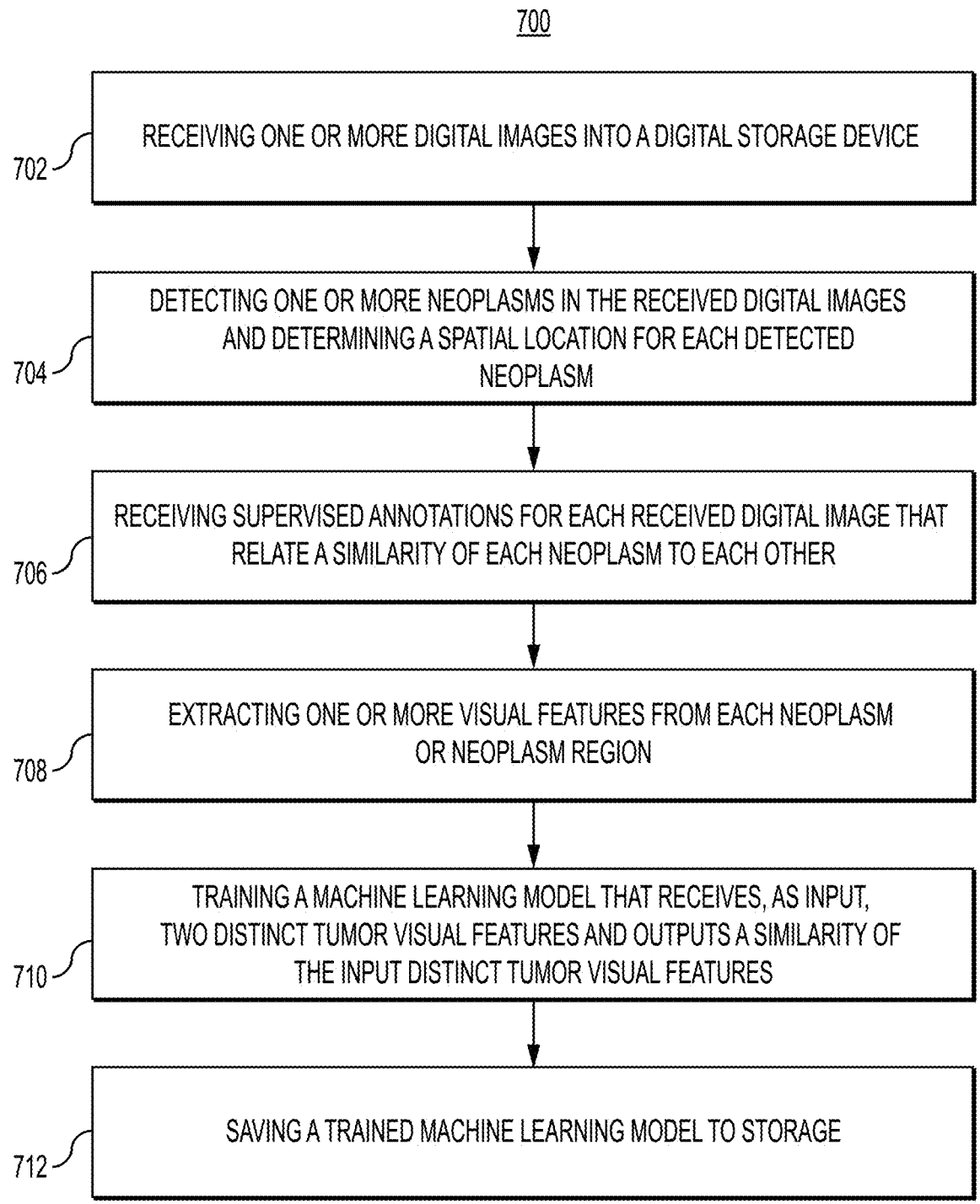
FIG. 7 is a flowchart of training a model for supervision of sub-clonal populations, according to an exemplary technique presented herein.

Referring to FIG. 7, a method of tumor clone identification using supervised learning of sub-clonal populations may include a method 700 of directly training a system or module (e.g., a machine learning system or module) using ground truth, i.e., verified, pixel-wise annotations of digital pathology images in a training dataset with respect to relationships among subclones. The ground truth annotations may be determined using any suitable method, such as, for example, spatial genomics, transcriptomics, or proteomics to detect, determine, or identify individual cells that belong to a same tumor and to measure a deviation among each tumor from each other to identify their evolutionary relationship. This identification may enable a tree to be created from the data. This approach is a gold standard. However, obtaining the data for the relationships among tumor populations for supervision may be time consuming, expensive, and difficult with conventional technology.

The method 700 of training the system may include a step 702 of receiving one or more digital pathology images (e.g., histology images or whole slide images) into a digital storage device (e.g., hard drive, network drive, cloud storage, RAM, etc.) for a collection of patients or other subjects. The method 700 of training the system may include a step 704 of determining, detecting, or identifying one or more (e.g., all) neoplasms on all received digital pathology images for each patient and determining a spatial location for each detected neoplasm. Step 704 may be performed using the Neoplasm Detection Module (e.g., neoplasm detection module 234).

The method 700 of training the system may include a step 706 of receiving supervised annotations for each received digital pathology image that relate a similarity of each neoplasm to each other, e.g., by genomic profiling each spatially distinct tumor population. The method 700 of training the system may include a step 708 of extracting visual features (e.g., embeddings) from each neoplasm or neoplasm region. This extraction may include using raw pixels and/or voxels or using a feature extractor for embeddings, such as a convolutional neural network (CNN) or a transformer, which may be trained with supervised or self-supervised learning. The visual information may be transformed or converted into a vector of features that represents each neoplasm.

The method 700 of training the system may include a step 710 of training a neural network for metric learning that receives, as input, two distinct tumor visual features (e.g., embeddings) and outputs a similarity of the input distinct tumor visual features. For example, the method may learn either a similarity score from raw pixel/voxel patches/regions or a vector embedding of those regions The similarity may be expressed in terms of genetics, proteomics, etc. This training may enable mapping of the visual features (e.g., embeddings) into a learned distance to measure how similar the visual features are in terms of genetics, proteomics, etc., rather than measuring only with a pre-specified (non-learned) distance metric. For example, such distance measurements may include measuring a semantic similarity between Gene Ontology (GO) terms derived from the visual features, a double-cut-and-join (DCJ) similarity measure, or similarity evaluation of DNA sequences based on frequent patterns and entropy, or any other suitable measurement. (See, for example, Zhao, C., Wang, Z. GOGO: An improved algorithm to measure the semantic similarity between gene ontology terms. Sci Rep 8, 15107 (2018), Rubert, D. Distance and Similarity Measures in Comparative Genomics, Faculdade de Computacao Universidade Federal de Mato Grosso do Sul (December 2019), and Xie, X., Guan, J. & Zhou, S. Similarity evaluation of DNA sequences based on frequent patterns and entropy. BMC Genomics 16 (Suppl 3), S5 (2015).) This neural network may be trained using all pair-wise embeddings in the received dataset of ground truth annotations. The method 700 of training the system may include a step 712 of saving or storing a learned metric (e.g., distance metric) to a disk or other storage device, such as the digital storage device in which the digital pathology images are received.

Figure 8:
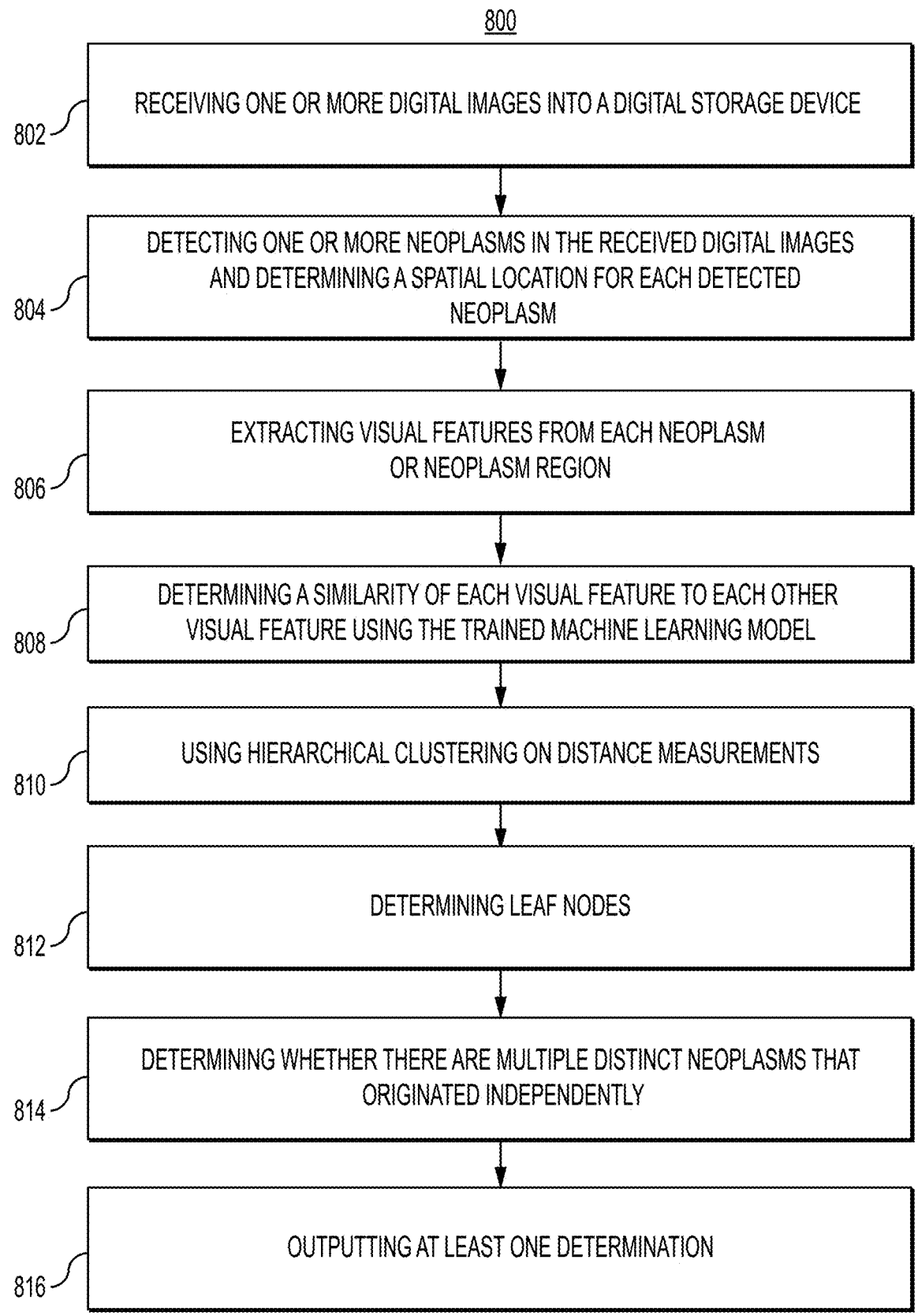
FIG. 8 is a flowchart of using a model for supervision of sub-clonal populations, according to an exemplary technique presented herein.

Referring to FIG. 8, a method 800 of using supervision of subclonal populations may include a step 802 of receiving one or more digital pathology images (e.g., histology images or whole slide images) into a digital storage device (e.g., hard drive, network drive, cloud storage, RAM, etc.) for a patient or other subject. The method 800 of using supervision of sub-clonal populations may include a step 804 of identifying, detecting, or determining one or more (e.g., all) neoplasms on all images for the patient and determining a spatial location for each detected neoplasm using, for example, the neoplasm detection module 234. The method 800 of using supervision of sub-clonal populations may include a step 806 of extracting visual features (e.g., embeddings) from each neoplasm or neoplasm region. This extraction may include using raw pixels and/or voxels or by using a feature extractor for embeddings such as a convolutional neural network or a transformer, which may be trained with supervised or self-supervised learning. The visual information may be transformed or converted into a vector of features that represents each neoplasm.

The method 800 of using supervision of subclonal populations may include a step 808 of determining a similarity of each visual feature to each other visual feature by, for example, applying or running a trained similarity metric system (e.g., a system trained using the training method 700) on all pair-wise combinations of visual features to determine how similar each visual feature (e.g., embedding) is to one another. That is, the method may include comparing image regions which have neoplasms in them and determining which neoplasms are most similar to one another and their evolutionary relationships. The method may produce a similarity matrix, where, for N neoplasm regions, an N×N similarity matrix may be determined describing how similar each neoplasm is to each other neoplasm. The method 800 of using supervision of subclonal populations may include a step 810 of using hierarchical clustering of neoplasms or neoplasm regions based on distance measurements. The distance measurements may have been received or determined or output by a previous step or system (e.g., a system that output the distance measurements to a hierarchy dendrogram). Step 810 may include any suitable method of hierarchical clustering such as, for example, agglomerative clustering, divisive clustering, or Ward's clustering method. If the relationships among neoplasms are not desired, but only determining some indication of the total number of neoplasm types then a non-hierarchical method may be used, such as k-means clustering.

The method 800 of using supervision of sub-clonal populations may also include a step 812 identifying or determining leaf nodes (e.g., leaf nodes 604 of FIG. 6) to analyze. The leaf nodes may be determined using the distance measurements and/or based on a hierarchy dendrogram, such as a hierarchy dendrogram previously output in a previous step or system. Step 812 may include thresholding a distance allowed in an embedding space and determining a leaf node when the distance is sufficiently low (e.g., less than a predetermined distance). The method 800 of using supervision of sub-clonal populations may include a step 814 of identifying or determining whether there are multiple (e.g., two or more) distinct neoplasms that originated independently. This determination may include "cutting" the hierarchy dendrogram at a top if the distance between to child node clusters is sufficiently large (e.g., greater than a predetermined distance) based on a threshold.

The method 800 of using supervision of sub-clonal populations may include a step 816 of outputting at least one determination to digital storage and/or a display. Step 816 may include outputting an analysis (e.g., by a machine learning system, the trained similarity metric system, neoplasm detection module 234, and/or tumor clone identification module 235), producing an output overlay on an image (e.g., the received digital pathology image) with each subclone population identified (e.g., with color coding, highlighting, shading, or other visual styles), and/or computing a most canonical form of each subclone (e.g., by identifying an embedding closest to an average within a cluster and then displaying that region for each subclone).

Using Supervision with Outcome or Treatment Response:

A method of using supervision with outcome or treatment response may include a step or method 900 of directly training a system or module (e.g., a scoring system) using ground truth, i.e., verified, annotations for each patient or subject based on an outcome for each patient (e.g., based on whether an outcome was poor or good with a same treatment). For example, the outcome may include survival time, progression-free survival time, tumor response measurements, or any other suitable measure. (See, for example, "Response evaluation criteria in solid tumors," https://en.wikipedia.org/wiki/Response_evaluation_criteria_in_solid_tumors.) The system may produce heterogeneous outcome information within an image, where different image regions may potentially indicate differing outcomes, which may indicate that distinct tumor populations may be present. For example, one tumor or tumor region may show a positive response to a treatment, such as, for example, reduced mass, reduced growth rate, etc., while another tumor or tumor region of the same patient may show a less positive response or no response at all. This may indicate, for example, that the tumor clones and/or subclones present in the first tumor or tumor region are more responsive to the treatment than the tumor clones and/or subclones present in the second tumor or tumor region.

Figure 9:
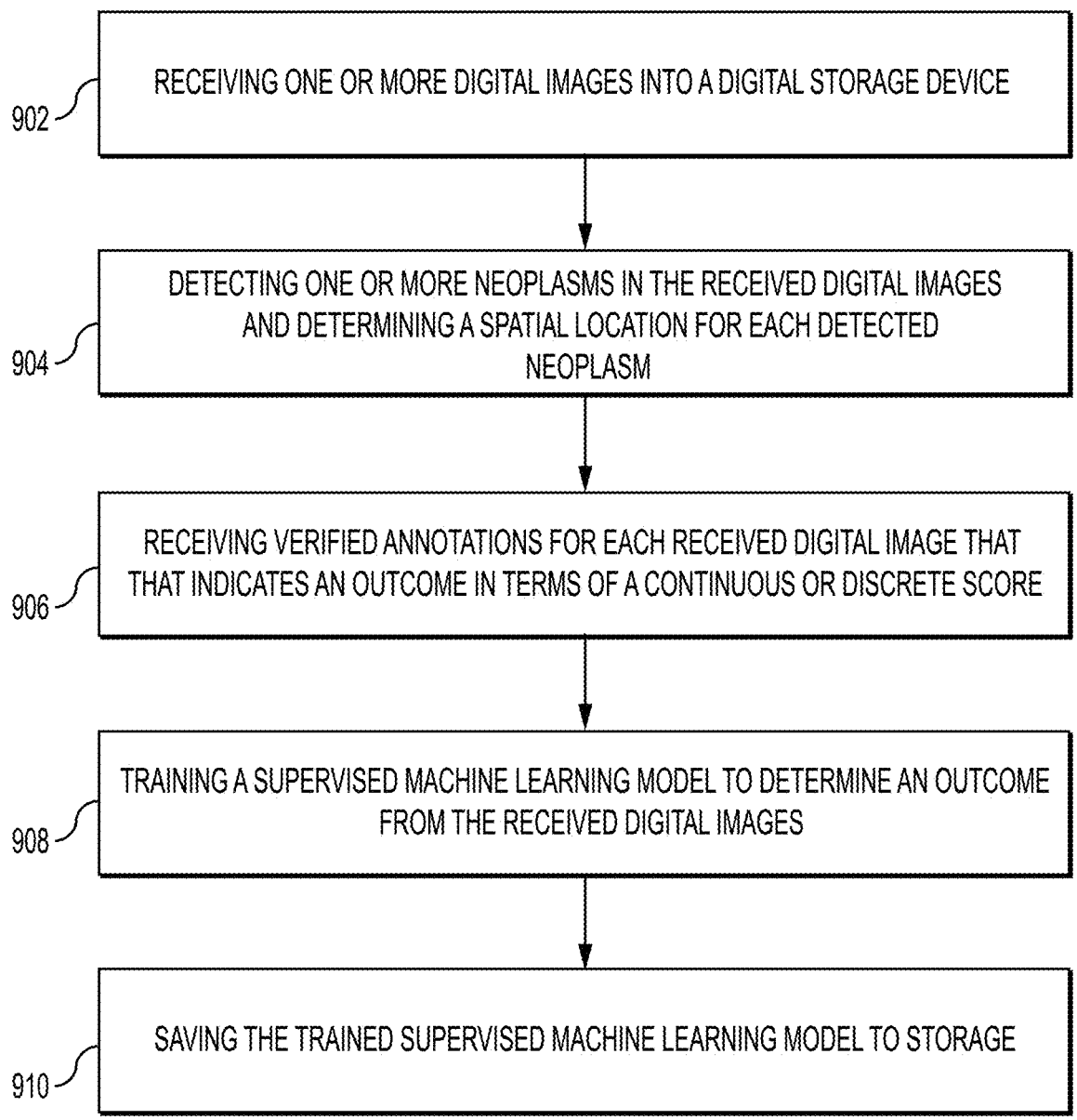
FIG. 9 is a flowchart of training a model for supervision with outcome or treatment response, according to an exemplary technique presented herein.

Referring to FIG. 9, the method 900 of training the system may include a step 902 of receiving one or more digital pathology images (e.g., histology images or whole slide images) into a digital storage device (e.g., hard drive, network drive, cloud storage, RAM, etc.) for a collection of patients or subjects. The method 900 of training the system may include a step 904 of determining, detecting, or identifying all neoplasms on the received digital pathology images (e.g., all images) for each patient and determining a spatial location for each detected neoplasm using, for example the Neoplasm Detection Module 234. The method 900 of training the system may include a step 906 of receiving ground truth, i.e., verified, annotations for each digital pathology image that indicates outcome, such as, for example, in terms of a continuous score (e.g., −10 to 10, where −10 may indicate a worst outcome and 10 may indicate a best outcome) or a discrete score (e.g., bad vs. good).

The method 900 of training the system may include a step 908 of training a supervised machine learning system (e.g., a convolutional neural network or CNN, transformer, multilayer perceptron or MLP, etc.) to determine an outcome for each patient from the received digital pathology images. This training step 908 may include extracting visual features (e.g., embeddings) from each neoplasm or neoplasm region and then aggregating them, or alternatively in an end-to-end manner to determine or infer outcomes directly from the digital pathology images, such as by using methods described in U.S. application Ser. No. 17/399,422, filed Aug. 11, 2021 (published as US Patent Application Publication No. 2022/005104), which is incorporated by reference herein, for inferring outcome. The method 900 may include a step 910 of saving or storing the trained machine learning system to storage such as a disk or other digital storage.

Figure 10:
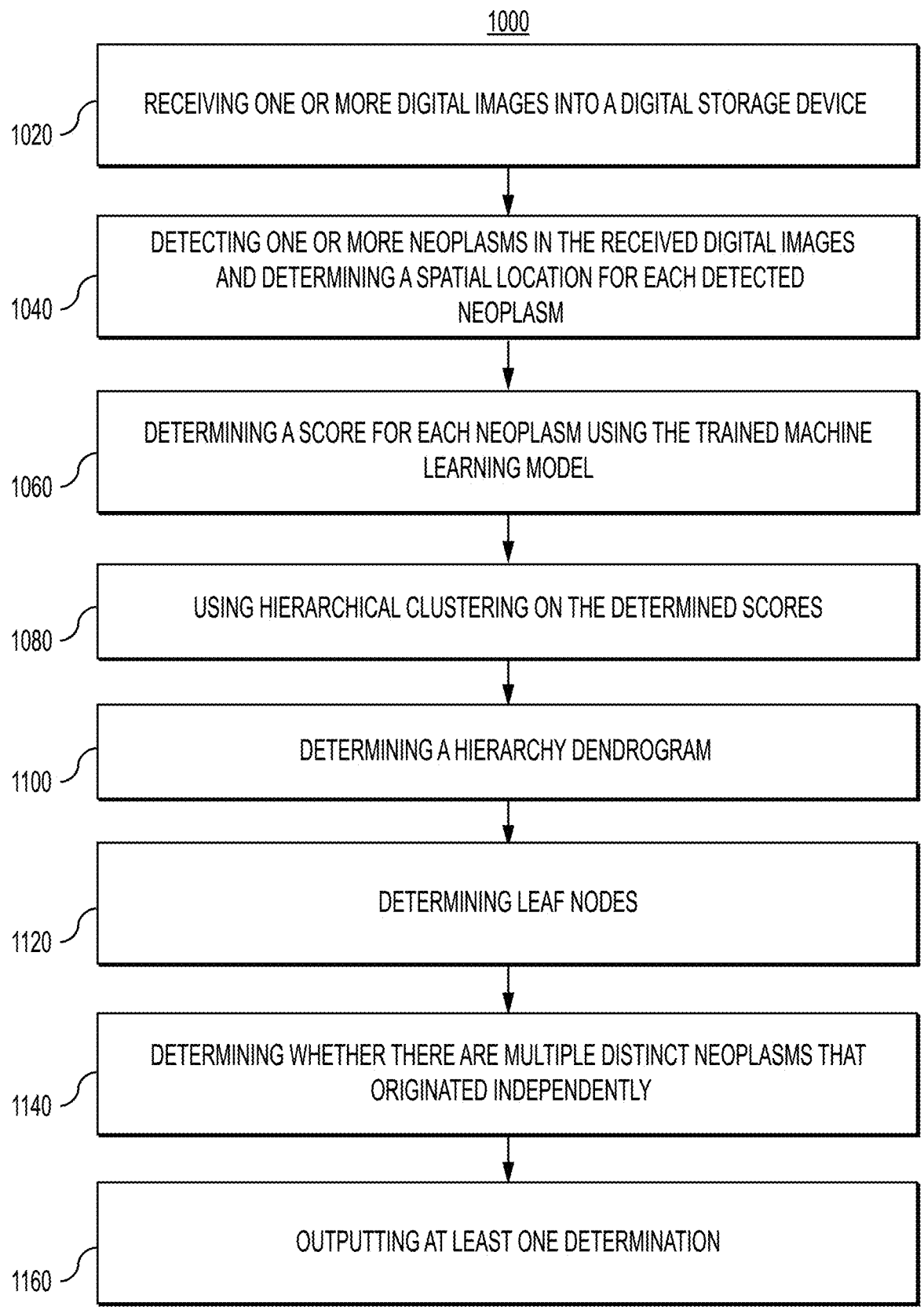
FIG. 10 is a flowchart of using a model for supervision with outcome or treatment response, according to an exemplary technique presented herein.

Referring to FIG. 10, a method 1000 of using supervision with outcome or treatment response may include a step 1020 of receiving one or more digital pathology images (e.g., histology images or whole slide images) into a digital storage device (e.g., hard drive, network drive, cloud storage, RAM, etc.) for a patient or other subject. The method 100 of using supervision with outcome or treatment response may include a step 1040 of determining, detecting, or identifying all neoplasms on the one or more received images (e.g., all images) for the patient and determining a spatial location for each detected neoplasm using, for example, the neoplasm detection module 234.

The method 1000 of using supervision with outcome or treatment response may include a step 1060 of determining a score for each neoplasm by, for example, applying or running a trained scoring system (e.g., such as a system trained using method 900). The determined score may correspond to an outcome or treatment response or a predicted outcome or treatment response, and step 1060 may include applying the trained scoring system to determine outcomes on each neoplasm such that each neoplasm may receive its own score (e.g., good outcome vs. bad outcome). FIGS. 11A and 11B, discussed in detail below, depict images of neoplasms from a patient for which some neoplasms indicate a likelihood of a good outcome and other neoplasms indicate a likelihood of a negative outcome. Step 1060 may also include determining a score or outcome for the patient overall based on one or more determined scores for one or more detected neoplasms.

The method 1000 of using supervision with outcome or treatment response may include a step 1080 of using hierarchical clustering on the determined or output scores. The scores may be combined with visual features, such as embeddings, extracted from each neoplasm for the purposes of hierarchical clustering, such as to allow further refinement of the hierarchical clustering to take into account both outcome and features of the neoplasms. Clustering step 1080 may include, for example, agglomerative clustering, divisive clustering, or Ward's clustering method. The method 1000 may include a step 1100 of determining and/or outputting a hierarchy dendrogram based on the determined stores and/or the clustering.

The method 1000 of using supervision with outcome or treatment response may include may include a step 1120 of determining or identifying leaf nodes (e.g., leaf nodes 604 of FIG. 6) in which to analyze. Step 1120 may be based on the hierarchy dendrogram and/or include thresholding a distance allowed in an embedding space and by considering a leaf node if the distance is sufficiently low (e.g., below a predetermined distance).

The method 1000 of using supervision with outcome or treatment response may include a step 1140 of determining or identifying whether there are multiple distinct neoplasms that originated independently. This determination may include "cutting" the hierarchy dendrogram at a top if a distance between two child node clusters is sufficiently large (e.g., greater than a predetermined distance) based on a threshold. Step 1140 may also include determining or identifying subclone populations based on the detected neoplasms, leaf nodes, distance measurements, and/or hierarchy dendrogram.

The method 1000 of using supervision with outcome or treatment response may include a step 1160 of outputting at least one determination to a display and/or storage (e.g., digital storage), such as an analysis or outcome for a patient (e.g., by a machine learning system, by the trained scoring system, neoplasm detection module 234, and/or by the tumor clone identification module 235), an output overlay on an image (e.g., the received digital pathology image) with each subclone population identified (e.g., with color coding, highlighting, shading, or other visual styles), and/or computing a most canonical form of each subclone. Computing the most canonical form of each subclone may include identifying an embedding closest to an average within the cluster and then displaying that region for each subclone.

Referring to FIGS. 11A and 11B, systems disclosed herein to predict an outcome or treatment response may provide a system that analyzes or operates on a collection of digital pathology images, such as, for examples, whole slide images (WSIs) of breast cancer data for a patient. After training to infer an outcome (i.e., severity of cancer), the system may output distinct neoplasm populations for a patient. Both FIG. 11A and FIG. 11B depict neoplasms from digital pathology images for the same patient. However, the population of neoplasms shown in FIG. 11A, including neoplasm 1170, indicate a good outcome, while the neoplasms shown in FIG. 11B, including neoplasm 1180, indicate a bad outcome. Current theory postulates that some of the population shown in FIG. 11A evolved to become malignant and gave rise to the population shown in FIG. 11B. Subsequently, hierarchical clustering may be used on the outcome scores and visual embeddings of each neoplasm to produce a dendrogram (e.g., FIG. 6) of the subclonal relationships among neoplasms.

Identifying Distinct Subclones

Techniques disclosed herein may be used to identify distinct subclones or to identify each subclone of a tumor. Such techniques may include running the disclosed systems and methods in any of the configurations described above.

Identifying Outcome Risk for Each Population

Techniques disclosed herein may be used to identify outcome risk for each population by identifying each subclonal population and then identifying or determining a severity of disease within each population. Such techniques may include training a system using supervision with outcome or treatment response, such as described above with respect to method 900.

Inferring Tumor Evolution

Techniques disclosed herein may be used to infer or determine relationships among subclones to determine how the subclones evolved. Such techniques may be used in any of the above-described configurations in training the system. For example, using supervision from spatial genomics/proteomics to infer or determine relationships among subclones may produce good or accurate results.

Figure 12:
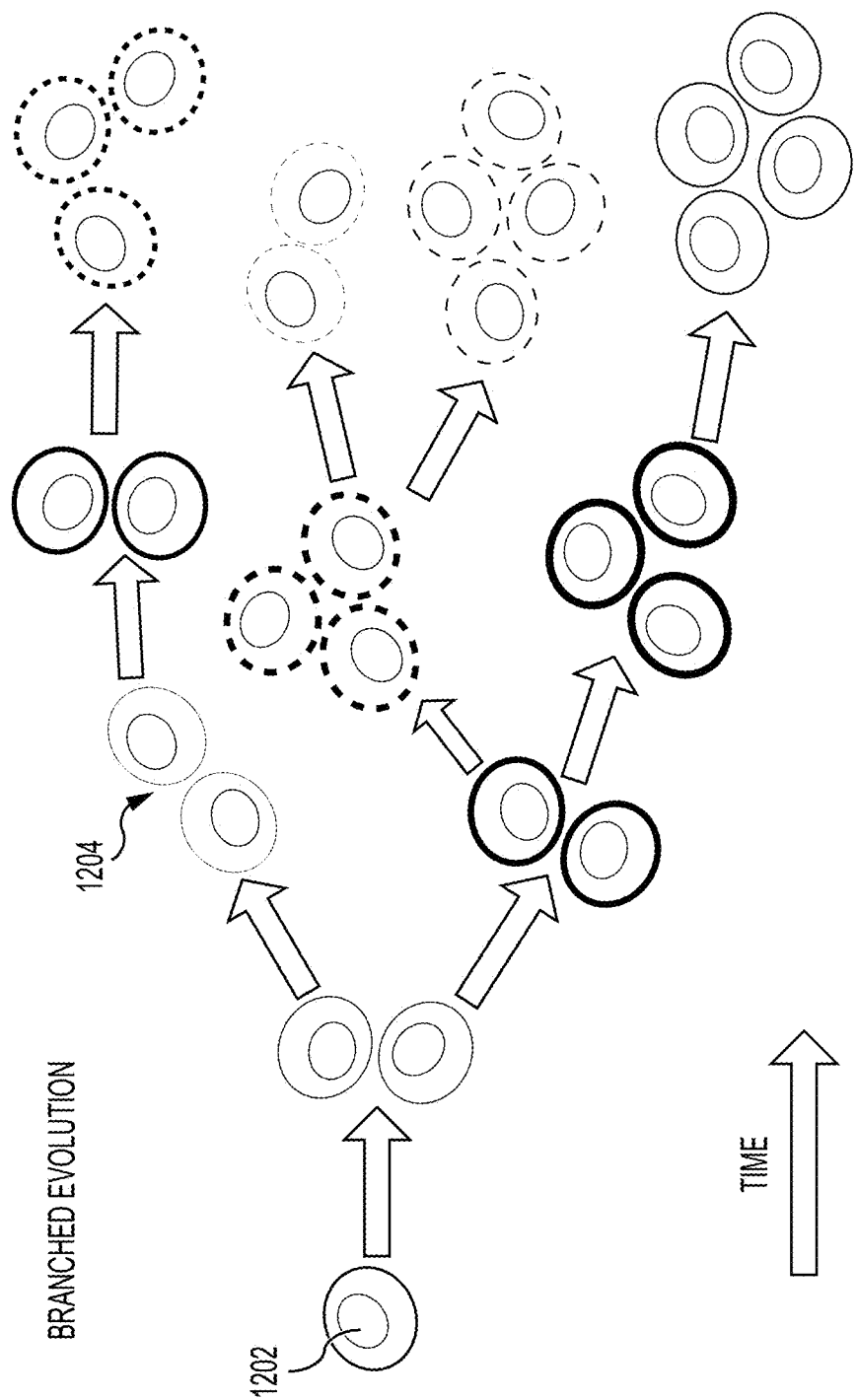
FIG. 12 illustrates a branched evolution of neoplasms.

Referring to FIG. 12, subclonal populations of a tumor may start with an original neoplastic cell 1202 and gradually evolve into different sub-populations (e.g., sub-population 1204). Techniques disclosed herein may be used to construct likely graphs of the tumor's evolution based on the tumor's characteristics, such as the branched evolution graph in FIG. 12. (FIG. 12 adapted from "Tumour heterogeneity—Wikipedia" (https://en.wikipedia.org/wiki/Tumour_heterogeneity).)

Identifying Optimal Treatment Options

Figure 13:
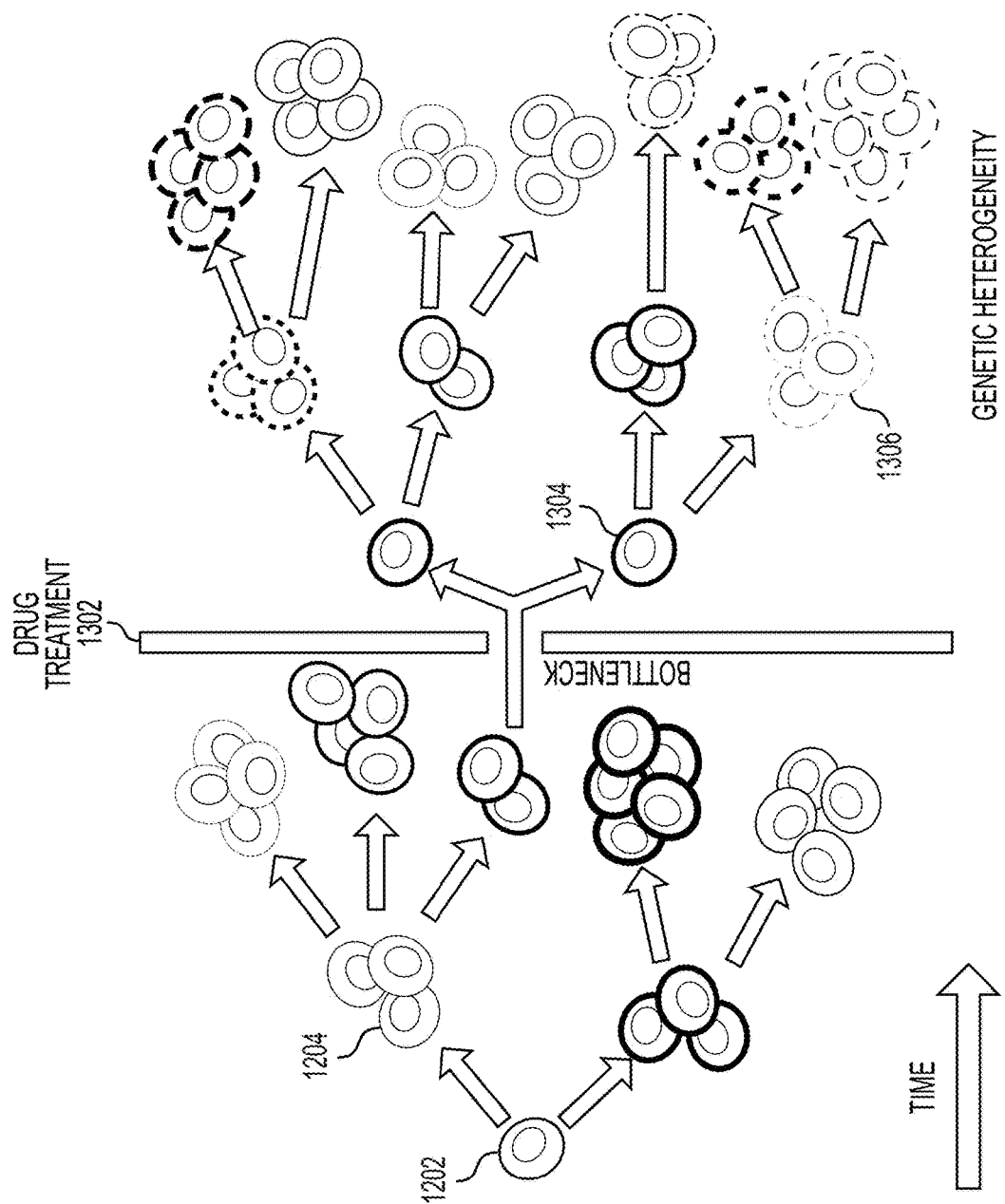
FIG. 13 illustrates treatment resistance of a tumor.

Referring to FIG. 13, heterogenic tumors may exhibit distinct sensitivities to various treatments, with some populations being resistant to some treatments. This sensitivity makes choosing an optimal treatment difficult because if a treatment is only effective for one subclone, but other subclones are present, cancer may not be eradicated by the treatment.

As shown in FIG. 13, a drug treatment that may only attack and/or treat a specific population of tumor subclones while leaving others unaffected may not eliminate a disease, as unaffected subclones with resistance to the treatment (e.g., subclones 1302) may continue to spread. Often, a portion of a tumor that remains is more aggressive. A best or most effective treatment across subclones may be identified or determined to increase or maximize a likelihood of curing a patient's disease or cancer. (FIG. 13 adapted from "Tumour heterogeneity-Wikipedia" (https://en.wikipedia.org/wiki/Tumour_heterogeneity).)

Techniques disclosed herein may be used to determine or identify the subclones and then infer or determine effective (and/or the most effective) treatment(s) for each subclone. A list of treatments across subclones may be integrated to identify effective (and/or the most effective) treatment(s) to eliminate all of the tumor subclones.

To determine effective treatments, each subclonal population may be fed into a machine learning system trained to infer optimal treatments for that distinct population (rather than and/or in addition to being operated on an entire population in aggregate). For example, techniques disclosed in U.S. patent application Ser. No. 17/399,422, filed Aug. 11, 2021; Ser. No. 17/391,997, filed Aug. 2, 2021 (published as US Patent Application Publication No. 2022/0044397 and issued as U.S. Pat. No. 11,308,616); and Ser. No. 17/160,127, filed Jan. 27, 2021 (published as US Patent Application Publication No. 2021/0233236 and issued as U.S. Pat. No. 11,182,900), which are incorporated herein by reference, may be used. After producing a list of viable treatments for each population, the treatment or treatments that would be most effective across all populations may be given to and/or used with the patient.

Referring to FIG. 14, a device 1400 may include a central processing unit (CPU) 1420. CPU 1420 may be any type of processing device including, for example, any type of special purpose or a general-purpose microprocessor device. As will be appreciated by persons skilled in the relevant art, CPU 1420 also may be a single processor in a multi-core/multiprocessor system, such system operating alone, or in a cluster of computing devices operating in a cluster or server farm. CPU 1420 may be connected to a data communication infrastructure 1410, for example a bus, message queue, network, or multi-core message-passing scheme.

Device 1400 may also include a main memory 1440, for example, random access memory (RAM), and may also include a secondary memory 1430. Secondary memory 1430, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 1430 may include similar means for allowing computer programs or other instructions to be loaded into device 1400.

Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 1400.

Device 1400 also may include a communications interface ("COM") 1460. Communications interface 1460 allows software and data to be transferred between device 1400 and external devices. Communications interface 1460 may include a model, a network interface (such as an Ethernet card), a communications, a PCMCIA slot and card, or the like. Software and data transferred via communications interface 1460 may in the form of signals, which may be electronic, electromagnetic, optical or other signals capable of being received by communications interface 1460. These signals may be provided to communications interface 1460 via a communications path of device 1400, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 1400 may also include input and output ports 1450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other techniques of the invention will be apparent to those skilled in the art from consideration of the specification and practice of the invention disclosed herein. It is intended that the specification and examples to be considered as exemplary only.

What is claimed is:

1. A computer-implemented method for detecting tumor subclones, the method comprising: receiving one or more digital images into a digital storage device, the one or more digital images including images of a tumor of a patient; detecting one or more neoplasms in the one or more received digital images for each patient; extracting one or more visual features from each detected neoplasm; determining a hierarchy dendrogram based on the detected one or more neoplasms and the extracted one or more visual features for each of the detected one or more neoplasms; determining one or more leaf nodes based on the determined hierarchy dendrogram; determining, based on the determined hierarchy dendrogram, whether there are two or more neoplasms among the detected one or more neoplasms that originated independently; and displaying and/or storing the determined two or more neoplasms.

2. The method of claim 1, further comprising determining a spatial location for each neoplasm or a determined neoplasm region, wherein determining the hierarchy dendrogram is further based on the determined spatial location.

3. The method of claim 1, further comprising using hierarchical clustering on the extracted one or more visual features, wherein determining the hierarchy dendrogram is based on the hierarchical clustering.

4. The method of claim 1, further comprising determining a similarity of each extracted visual feature to each other extracted visual feature.

5. The method of claim 4, wherein determining the similarity includes applying a trained similarity metric system on all pair-wise combinations of the one or more extracted visual features.

6. The method of claim 1, further comprising determining a score for each detected neoplasm, wherein determining the hierarchy dendrogram is further based on the determined score for each detected neoplasm.

7. The method of claim 6, wherein determining the score includes applying a trained scoring system.

8. The method of claim 6, wherein the score corresponds to an outcome or treatment response.

9. The method of claim 6, further comprising using hierarchical clustering on the determined score for each detected neoplasm, wherein determining the hierarchy dendrogram is further based on the hierarchical clustering.

10. The method of claim 1, further comprising dividing each received digital image into sub-regions, and determining which sub-regions among the divided sub-regions include a neoplasm.

11. The method of claim 1, further comprising determining a type for each detected neoplasm.

12. The method of claim 1, wherein detecting one or more neoplasms in the one or more received digital images for each patient is performed using a trained machine learning model.

13. The method of claim 1, further comprising outputting the hierarchy dendrogram on a display.

14. The method of claim 13, further comprising determining that two or more neoplasms among the detected one or more neoplasms originated independently, wherein the output hierarchy dendrogram is color coded based on the determined two or more neoplasms that originated independently.

15. A system for detecting tumor subclones, the system comprising: a data storage device storing instructions for detecting tumor subclones in an electronic storage medium; and a processor configured to execute the instructions to perform a method including: receiving one or more digital images into a digital storage device, the one or more digital images including images of a tumor of a patient; detecting one or more neoplasms in the one or more received digital images for each patient; extracting one or more visual features from each detected neoplasm; determining a hierarchy dendrogram based on the detected one or more neoplasms and the extracted one or more visual features for each of the detected one or more neoplasms; determining one or more leaf nodes based on the determined hierarchy dendrogram; determining, based on the determined hierarchy dendrogram, whether there are two or more neoplasms among the detected one or more neoplasms that originated independently; and displaying and/or storing the determined two or more neoplasms.

16. The system of claim 15, wherein the system is further configured for:
using hierarchical clustering on the extracted one or more visual features, wherein determining the hierarchy dendrogram is based on the hierarchical clustering.

17. The system of claim 15, wherein detecting one or more neoplasms in the one or more received digital images for each patient is performed using a trained machine learning model.

18. A non-transitory machine-readable medium storing instructions that, when executed by a computing system, causes the computing system to perform a method for detecting tumor subclones, the method including: receiving one or more digital images into a digital storage device, the one or more digital images including images of a tumor of a patient; detecting one or more neoplasms in the one or more received digital images for each patient; extracting one or more visual features from each of the detected one or more neoplasms; determining a hierarchy dendrogram based on the detected one or more neoplasms and the extracted one or more visual features for each detected neoplasm; determining one or more leaf nodes based on the determined hierarchy dendrogram; determining, based on the determined hierarchy dendrogram, whether there are two or more neoplasms among the detected one or more neoplasms that originated independently; and displaying and/or storing the determined two or more neoplasms.

19. The non-transitory machine-readable medium of claim 18, the method further comprising:
using hierarchical clustering on the extracted one or more visual features, wherein determining the hierarchy dendrogram is based on the hierarchical clustering.

20. The non-transitory machine-readable medium of claim 18, wherein detecting one or more neoplasms in the one or more received digital images for each patient is performed using a trained machine learning model.

* * * * *